US010161948B2

(12) United States Patent
Vacic et al.

(10) Patent No.: US 10,161,948 B2
(45) Date of Patent: Dec. 25, 2018

(54) PERFORMING ANTIMICROBIAL SUSCEPTIBILITY TESTING AND RELATED SYSTEMS AND METHODS

(71) Applicant: SELUX DIAGNOSTICS, INC., Watertown, MA (US)

(72) Inventors: Aleksandar Vacic, Watertown, MA (US); Nathan Purmort, Watertown, MA (US); Eric Stern, Watertown, MA (US); Anna Passernig, Los Gatos, CA (US); Paul Otten, Los Gatos, CA (US); Randy Tragni, Los Gatos, CA (US); Ronan Hayes, Los Gatos, CA (US); Andriy Tsupryk, Los Gatos, CA (US); Bruce Richardson, Los Gatos, CA (US)

(73) Assignee: SELUX DIAGNOSTICS, INC., Charlestown, MA (US)

( * ) Notice: Subject to any disclaimer, the term of this patent is extended or adjusted under 35 U.S.C. 154(b) by 0 days.

(21) Appl. No.: 15/829,710

(22) Filed: Dec. 1, 2017

(65) Prior Publication Data

US 2018/0088141 A1 Mar. 29, 2018

Related U.S. Application Data

(63) Continuation of application No. PCT/US2017/028906, filed on Apr. 21, 2017.
(Continued)

(51) Int. Cl.
*C12M 1/34* (2006.01)
*G01N 35/02* (2006.01)
(Continued)

(52) U.S. Cl.
CPC ............ *G01N 35/02* (2013.01); *B01J 20/041* (2013.01); *C12Q 1/18* (2013.01); *G01N 21/01* (2013.01);
(Continued)

(58) Field of Classification Search
CPC ...................................... G01N 35/02
See application file for complete search history.

(56) References Cited

U.S. PATENT DOCUMENTS 5,346,303 A * 9/1994 Heinonen ........... B01F 11/0014
366/208
5,885,791 A 3/1999 Cutler et al.
(Continued)

FOREIGN PATENT DOCUMENTS

EP 3121262 A1 1/2017
WO 01-60519 A1 8/2001
(Continued)

*Primary Examiner* — William H. Beisner

(57) ABSTRACT

In some aspects, automated rapid antimicrobial susceptibility testing systems for performing a multi-assay testing sequence can include an automated incubation assembly having a nest assembly adapted to house at least one test panel having a plurality of wells for receiving a sample comprising microorganisms originating from a clinical sample, the incubation assembly facilitating incubation of one or more test panels in order to undergo the multi-assay testing sequence; a robotic handling assembly configured to accept one or more incoming test panels and move them to and from the incubation assembly for incubation between each assay of the multi-assay testing sequence; an automated liquid handling assembly configured to exchange one or more fluids in the plurality of wells of the test panels; and an optical assembly for interrogation and readout of each assay of the multi-assay testing sequence being performed in the plurality of wells.

21 Claims, 19 Drawing Sheets

Related U.S. Application Data

(60) Provisional application No. 62/326,525, filed on Apr. 22, 2016, provisional application No. 62/393,936, filed on Sep. 13, 2016.

(51) Int. Cl.
  *B01J 20/04* (2006.01)
  *C12Q 1/18* (2006.01)
  *G01N 21/01* (2006.01)
  *G01N 35/00* (2006.01)
  *G01N 35/10* (2006.01)
  *C12M 1/00* (2006.01)
  *C12M 1/26* (2006.01)
  *C12M 1/36* (2006.01)
  *G01N 35/04* (2006.01)

(52) U.S. Cl.
  CPC ......... *G01N 35/00* (2013.01); *G01N 35/0099* (2013.01); *G01N 35/028* (2013.01); *G01N 35/1065* (2013.01); *C12M 33/10* (2013.01); *C12M 41/36* (2013.01); *C12M 41/48* (2013.01); *C12M 47/02* (2013.01); *G01N 2021/0112* (2013.01); *G01N 2035/00118* (2013.01); *G01N 2035/00237* (2013.01); *G01N 2035/00346* (2013.01); *G01N 2035/00356* (2013.01); *G01N 2035/00465* (2013.01); *G01N 2035/00485* (2013.01); *G01N 2035/00524* (2013.01); *G01N 2035/00841* (2013.01); *G01N 2035/0425* (2013.01)

(56) References Cited

U.S. PATENT DOCUMENTS

| | | | |
|---|---|---|---|
| 7,270,784 B2 * | 9/2007 | Vuong | G01N 35/028 422/105 |
| 2002/0064867 A1 | 5/2002 | Clark et al. | |
| 2003/0082551 A1 * | 5/2003 | Zarling | C12N 15/1079 435/6.16 |
| 2005/0095665 A1 | 5/2005 | Williams et al. | |
| 2010/0124763 A1 | 5/2010 | Walsh et al. | |
| 2010/0203573 A1 * | 8/2010 | Heinonen | G01N 35/028 435/29 |
| 2017/0096631 A1 | 4/2017 | Uematsu et al. | |

FOREIGN PATENT DOCUMENTS

WO   WO-2014167173 A1 * 10/2014 .......... B01F 11/0014
WO   2015-141040 A1     9/2015

* cited by examiner

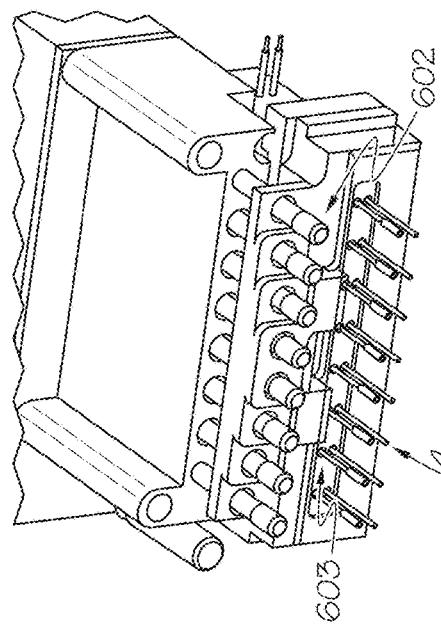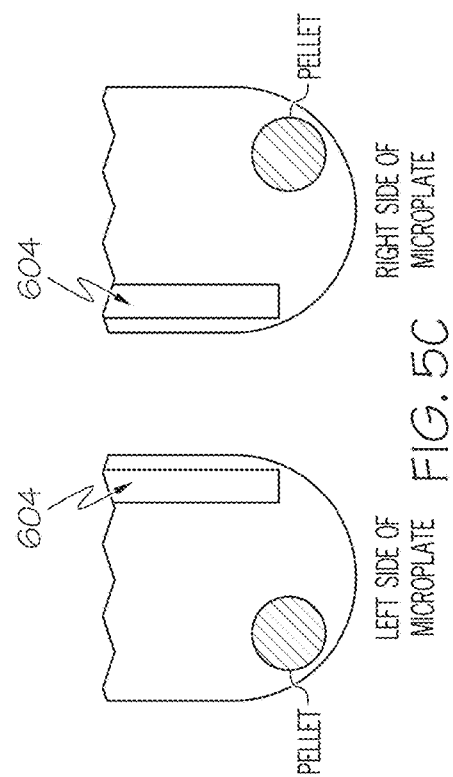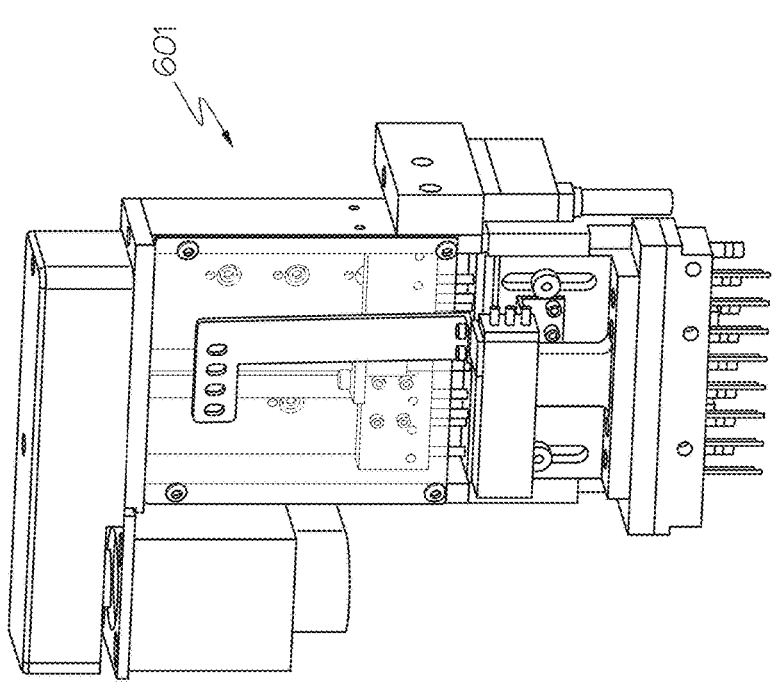

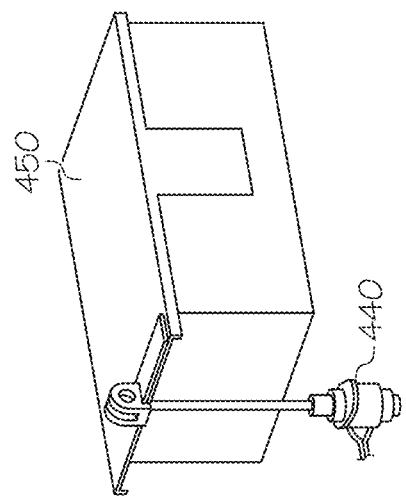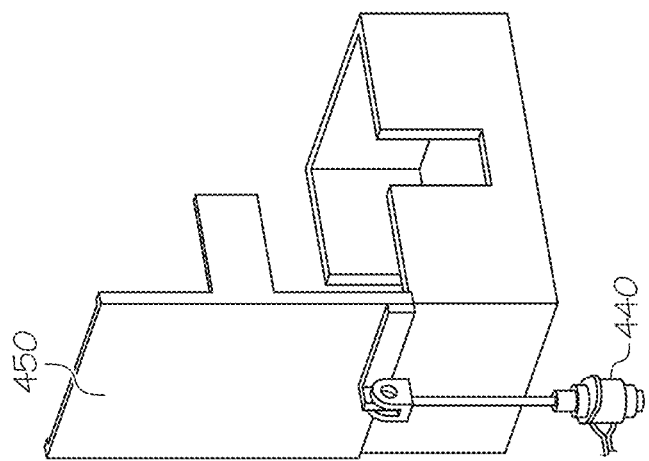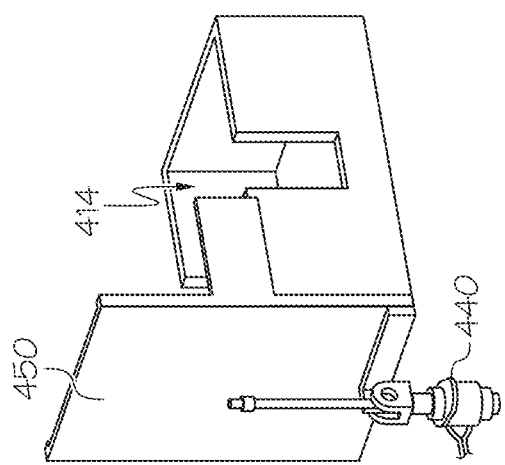

PERFORMING ANTIMICROBIAL SUSCEPTIBILITY TESTING AND RELATED SYSTEMS AND METHODS

RELATED APPLICATIONS

This application is a continuation of International Patent Application No. PCT/US17/28906, filed on Apr. 21, 2017, and titled "Performing Antimicrobial Susceptibility Testing and Related Systems and Methods." PCT/US17/28906 designates the United States and claims priority to and the benefit of U.S. Provisional Patent Application Ser. No. 62/326,525, filed Apr. 22, 2016, titled "Device for Rapid Antibiotic Susceptibility Testing," and the benefit of U.S. Provisional Patent Application Ser. No. 62/393,936, filed Sep. 13, 2016, titled "Device for Rapid Antibiotic Susceptibility Testing." The contents of all of the aforementioned patent applications are hereby incorporated herein by reference in their entireties.

TECHNICAL FIELD

This disclosure relates generally to antimicrobial susceptibility testing, and more specifically to performing automated rapid antimicrobial susceptibility testing and related systems and methods.

BACKGROUND

Antimicrobials have transformed the practice of medicine, making once lethal infections more easily treatable and saving millions of lives. Quick administration of antimicrobials has been proven to reduce mortality especially in severe cases such as septicemia. In these severe cases, the most potent antimicrobials are used since information about organism (e.g., species) is typically not known. These broad-spectrum antimicrobials can have serious side effects, cause organ damage, prolong recovery and hospital stays, and in some cases increase mortality. Furthermore, the overuse of antimicrobials has caused the rise of antimicrobial resistant organisms, which have become a serious and growing threat to public health. A growing body of evidence demonstrates that Antibiotic Stewardship Programs can optimize the treatment of infections and reduce adverse effects associated with antimicrobial use and misuse together with increased cure rates, reduced treatment failures, and increased percentage of correct therapy. By using targeted antimicrobial therapy, patient mortality can be reduced (e.g., minimized), recovery can be shortened, and hospitals can save money on both patient stay and minimizing usage of expensive antimicrobials.

However, complete information typically needed for targeted antimicrobial therapy is typically delivered 2-3 days after a sample is taken. Current antimicrobial susceptibility tests (AST) may require more than 8 hours to determine and deliver relevant and useful information, which is typically not sufficient to provide a same day result. In an often best case scenario, this can cause antimicrobial therapies to be adjusted the following day.

Some systems perform phenotypic testing of pathogenic organisms by exposing them to a set of antimicrobial dilution series and measuring their growth over time. Growth can be measured indirectly and most frequently optically by measuring solution turbidity or fluorescence of a dye triggered by microorganism metabolism. By quantitative comparison of optical signal, these systems determine the lowest concentration in dilution series of each antimicrobial that successfully inhibits growth of the tested microorganism. This value, known as minimum inhibitory concentration (MIC), is often used by clinicians to determine the most effective antimicrobial and dosage, i.e., deliver targeted antimicrobial therapy. In addition, qualitative susceptibility result (QSR) in form of susceptible (S), intermediate (I) and resistant (R) may be reported with or instead of MIC.

Historically, automation in microbiology clinical laboratories has been slow compared to clinical chemistry and hematology areas where automation and new assay development have reduced time from sample to result. Three commonly used systems have been developed in the past 30 years and were designed to automate operation typically done by highly trained technicians.

To perform a phenotypic test, one measures growth dependence of a given microorganism in standardized nutrient broth (e.g., Muller Hinton broth) and in presence of antimicrobial. Antimicrobials can be prepared as 2× dilution series. Manually, growth is typically measured only once, after 16-24 hours, as defined by Clinical & Laboratory Standards Institute (CLSI). Some automated systems, as previously mentioned, shorten this time by interrogating microorganism growth in each test well periodically (e.g., 20 minutes). This process can be tedious and is typically not performed by technicians. Growth curves are then analyzed using proprietary algorithms that include analysis of absolute, relative values between wells, rates, integrals, etc., of growth curves.

SUMMARY

In some aspects, the systems and methods described herein can help provide a solution for achieving high-sensitivity, rapid (e.g., same-shift) antimicrobial susceptibility testing results by utilizing end point assays based on amplification of microorganism presence that allow for detection of minute differences of growth and measure effects of antimicrobials faster than traditional methods, such as those involving optical density, nephelometry, or fluorometry. Moreover, the systems and methods herein can allow for detection of filamentous growth by utilizing surface as a proxy for microorganism growth rather than approaches involving metabolic dye or light scattering and absorption. Moreover, the systems and methods herein can allow for AST results for slow-growing species and strains to be obtained by delaying the onset of the end-point growth assay until sufficient microorganism growth for accurate results has been observed.

Typically, high sensitivity assays that are based on amplification (e.g., catalytic) can be performed only once since chemistries necessary for those assays usually destroy the target microorganism. Thus, the systems and methods described herein typically use two types of assays to address this issue. In some cases, a preliminary (e.g., checkpoint) assay can be performed first and can be repeated periodically to interrogate growth of uninhibited microorganisms (i.e., without antibiotic presence). These checkpoint assays can be performed in wells referred to herein as control wells. Examples of typical control wells are a growth well containing microorganisms in nutrient broth and a contamination control well containing nutrient broth only. The system interrogates growth/no growth optically (e.g., absorbance, fluorescence metabolic dye, etc.) and once a particular ratio and/or kinetic change between the control wells is achieved and detected, one or more end point assays (e.g., an amplification assay or growth assay) can be initiated on samples disposed in other portions of the test panel (e.g., the rest of, or the entire, test panel). The samples, for example, can include microorganisms originating from a clinical sample. Additional wells, such as wells containing microorganisms in saline or other media that does not promote growth of microorganisms (i.e., due to lack of nutrients) can be utilized for growth check and MIC determination. These wells can contain concentrations of microorganisms that are similar to the starting sample and referred to as "frozen in time" (e.g., FIT) control.

In some cases, the systems and methods described herein can be implemented to provide faster testing than some conventional systems. For example, though some automated systems may speed time to obtain results, none are currently cleared to yield results within 5 hours, which can be the definition of "same-shift" results for many clinical laboratories. Because of this slow time-to-results and because AST results are complex and may utilize expert interpretation for clinical action, such conventional systems can result in a day delay between the onset of susceptibility testing and clinical action.

In some embodiments, an incubator chamber can be included to maintain an optimal growth temperature for the organism under test. Unlike other conventional systems, in some examples, the systems and methods herein can include an incubator that provides or otherwise allows agitation of test panels. In some cases, orbital shaking can improve oxygenation and can allow continuous and more uniform exposure of microorganisms to nutrients in growth medium. Agitation can further increase the uniformity of microorganism exposure to antimicrobial compounds. These may, in some cases, increase growth and shorten time needed to quantify MIC and/or QSR.

In some embodiments, the systems herein can include an optical system that can include an optical excitation source (e.g., xenon lamp, light emitting diode (LED)), a set of optical filters (e.g., discrete filters, monochromators) with desired characteristics (e.g., band-pass, band-stop, central wavelength, full width half max (FWHM)), and an optical detector (e.g., photomultiplier tube). The optical systems can also include data acquisition and processing electronics used to collect and process data. In some cases, the optical system can include one or more components, such as fiber optics and collection optics, nested in, or otherwise disposed within or on, a robotic arm used to move cartridges throughout the system. Such a configuration can help achieve a faster sample processing and time for results readout. These optics can carry a signal from cartridges to the detector and data processing electronics.

In yet another aspect, a liquid handling system can be included and used to deliver and/or remove (e.g., aspirate) reagents to and from the test wells within the cartridges.

In another aspect, a separation method can be included, which can be used to remove excess fluid from test wells that could interfere with the various assays performed. This step can be a part of the washing process step and can include one or more of various procedures, such as centrifugation, magnetic separation, or vacuum filtration. For example, in some embodiments, centrifugation separation can be used to separate (e.g., pellet) microorganisms. In some cases, the separation can be followed by an aspiration process step to remove supernatant fluid. In some embodiments, the term wash sequence can refer to a centrifugation, aspiration, and liquid buffer additional (e.g., assay or wash buffer).

In some aspects, automated rapid antimicrobial susceptibility testing systems for performing a multi-assay testing sequence can include: an automated incubation assembly comprising a nest assembly adapted to house at least one test panel (e.g., cartridge) having a plurality of wells for receiving a sample comprising microorganisms originating from a clinical sample, the incubation assembly facilitating incubation of one or more test panels in order to undergo the multi-assay testing sequence; a robotic handling assembly configured to accept one or more incoming test panels and move them to and from the incubation assembly for incubation between each assay of the multi-assay testing sequence; an automated liquid handling assembly configured to exchange one or more fluids in the plurality of wells of the test panels; and an optical assembly for interrogation and readout of each assay of the multi-assay testing sequence being performed in the plurality of wells.

Embodiments can include one or more of the following features.

In some embodiments, the systems can include a sample separation assembly configured to separate microorganisms from a remainder of the sample within the wells of test panel. For example, the sample separation assembly can form a pellet of the microorganisms within the wells of the test panels. The separation assembly can be a centrifugation system. The separation assembly can include a magnetic capture separation system. The separation assembly can include a vacuum filtration system.

The incubation assembly can be configured to agitate the test panel during incubation. The incubation assembly can include a drive system to agitate the nest assembly carrying the at least one test panel. The drive system can be configured to impart an orbital speed on the nest assembly that is variable. The speed can be between 100 and 650 RPM. A radius of an agitation orbit can be adjustable. A radius of an agitation orbit can be about 1 mm to about 10 mm.

The optical assembly can be mounted on or integrally formed within a robotic arm of the robotic handling assembly. The optical assembly can be configured to measure at least one of absorbance, fluorescence, luminescence, time-resolved fluorescence, or time-gated luminescence emitted from the sample during the multi-assay testing sequence. An excitation wavelength to generate a fluorescence emission can be about 560 nm and a wavelength of the emission can be about 590 nm. An excitation wavelength to generate a time-gated luminescence emission can be from about 280 nm to about 360 nm and a wavelength of the emission can be about 608 nm to about 623 nm. The optical assembly can include two or more optical filters for interrogation and readout of each assay of the multi-assay testing sequence being performed in the plurality of wells. Two optical filters can be disposed on an indexing component configured to selectively position a first optical filter in line with an excitation source and a second optical filter in line with an optical detector. The indexing component can include a second set of two filters, and where an indexing motion of the indexing component replaces the optical filter in-line with the excitation source and the optical filter in-line with the optical detector.

The fluid handling assembly can include a liquid addition system and an aspiration system. Reagents can be stored in a disposable container. The container can be disposed of and replaced after at least every shift, at least every 1 day, at least every 5 days, or at least every week. The container can be disposed of and replaced after at least every testing sequence, every 10 testing sequences, every 20 testing sequences, every 50 testing sequences, or every 100 testing sequences.

The system can be configured to process simultaneously at least 2, at least 4, at least 6, at least 8, at least 10, or at least 12 test panels. The system can be configured to yield a testing sequence throughput of at least 2, at least 4, at least 6, at least 8, at least 10, at least 12, at least 16, at least 20 test panels per hour. A time duration for processing a test panel through the testing sequence from insertion of the test panel into the system to obtaining a result can be less than 8 hours, less than 6 hours, less than 5 hours, less than 4 hours, less than 3 hours, or less than 2 hours.

In some aspects, methods for performing multi-assay rapid antimicrobial susceptibility testing sequences can include: inoculating a sample comprising a microorganism derived from a clinical sample into a plurality of wells of a test panel (e.g., a cartridge), at least a portion of the plurality of wells containing one or more antimicrobials of a plurality of antimicrobials for inoculation of the sample; loading the test panel into an automated rapid antimicrobial susceptibility testing system for performing a multi-assay testing sequence; and operating the testing system to: move the loaded test panel to an incubation assembly; incubate and agitate the inoculated sample in the incubation assembly; at least once, periodically measure an amount of sample growth in a plurality of control wells of the plurality of wells; responsive to determining that a level of growth in the control wells meets or exceeds a threshold level of growth, stop incubation; perform one or more end point assays on incubated samples in the test panel; measure an optical output from the sample in the plurality of wells of the test panel, the optical output corresponding to an amount of the microorganism remaining in each of the plurality of wells; and report at least one of: a minimum inhibitory concentration of and/or a qualitative susceptibility interpretation for the microorganism remaining in each of the plurality of wells and the plurality of antimicrobials.

Embodiments can include one or more of the following features.

The performing the end point assay can include one or more of: liquid handling, centrifugation, incubation, or shaking of the sample. The liquid handling can include performing one or more aspiration liquid addition steps.

The performing the end point assay can include a plurality of binding steps. An amplification species of the binding steps can include a catalyst. An amplification species of the binding steps can include a europium chelate.

The methods and testing systems can be configured to process simultaneously at least 2, at least 4, at least 6, at least 8, at least 10, or at least 12 test panels. The methods and testing systems can be configured to yield a testing sequence throughput of at least 2, at least 4, at least 6, at least 8, at least 10, at least 12, at least 16, at least 20 test panels per hour. A time duration for processing a test panel through the testing sequence from insertion of the test panel into the testing system to obtaining a result using the methods can be less than 8 hours, less than 6 hours, less than 5 hours, less than 4 hours, less than 3 hours, or less than 2 hours.

In some aspects antimicrobial susceptibility testing system sample cartridge handling devices can include: a robotic gripping portion having an interface configured to be coupled by a gripping mechanism of a robotic arm; and a set of lifting fingers sized and configured to support a sample cartridge, the lifting fingers defining a cartridge platform.

Embodiments can include one or more of the following features.

The set of fingers can include one or more cartridge positioning features that define the cartridge platform and limit the cartridge from sliding relative to the fingers. The cartridge positioning features can include vertical ridges.

The fingers can be laterally separated by at least about 3 inches. A distal end of at least one of the fingers can be tapered.

The interface of the robotic gripping portion can include a set of protrusions extending laterally to couple to the gripping mechanism of the robotic arm. A distal end of the gripping portion can be adjustable in width from at least about 3 inches to about 4 inches. The gripping mechanism can be operated at least in part by a linear actuator and linkage to articulate one or more gripping arms. The gripping mechanism can be operated at least in part by a linear spring mechanism in connection with linkage to articulate one or more gripping arms.

In some aspects, incubation systems for a sample testing system can include: a tiered frame configured comprising one or more floors, each floor comprising: a stage to accommodate a sample testing cartridge; one or more cartridge positioning features extending from the stage; and a set of recesses to accommodate a test cartridge handling device; and an agitation system configured to generate a repeated motion of the tiered frame.

Embodiments can include one or more of the following features.

The tiered frame can include multiple floors where each floor comprises two surfaces to accommodate two sample testing cartridges. The one or more cartridge positioning features can include a vertical ridge along a front or rear end of the stage to accommodate a testing cartridge. The floor can include a heating element disposed in or along the stage.

The agitation system can be configured to axially or orbitally agitate the frame. The agitation system can include a rotational agitation system having a rotating oscillating component. The agitation system can include a bearing surface along which the rotating oscillating component interfaces during rotation. The bearing surface can include a roller bearing. The rotating oscillating component can include a counter balance weight. The agitation system can include one or more linear actuators. The agitation system can include one or more linear bearing surfaces. The agitation system can include two linear bearing surfaces positioned substantially perpendicularly with respect to one another. The agitation system can include two linear bearing rails and sliding stages configured to slide along the bearing rails.

The agitation system can be configured to agitate the frame along an orbital path having a radius that is less than about 25 mm. The agitation system can be configured to agitate the frame along an orbital path having a radius that is from about 1 mm to about 12 mm. The agitation system can be configured to vary a radius of the orbital path of agitation. The agitation system can be configured to agitate the frame along an orbital path at a rate of greater than about 75 revolutions per minute. The agitation system can be configured to agitate the frame along an orbital path at a rate of about 150 revolutions per minute to about 650 revolutions per minute. The agitation system can be configured to vary the rate at which the frame travels along the orbital path of agitation.

The incubation system can include a cover along a front face of the frame. The frame can define a front opening along a front face and a rear opening along a rear face. The frame can be configured to receive a cartridge from a user through the front opening and the cartridge can be removed by a handling device of an automated system through the rear opening.

In some aspects, methods of aspirating fluid from one or more chambers in a cartridge can include: displacing one or more microorganisms suspended in the fluid within the chambers using a centrifugal force; and aspirating a first fluid from a first chamber from a location substantially opposite the displaced microorganisms with respect to a central region of the first chamber.

Embodiments can include one or more of the following features.

The displacing one or more microorganisms suspended in the fluid can include running the cartridge through a centrifugation system. The aspirating the first fluid from the first chamber can include disposing an aspiration nozzle of a fluid processing system coupled to robotic arm into the first chamber.

The methods can include aspirating a second fluid from a second chamber from a location substantially opposite a second set of displaced microorganisms with respect to a central region of the second chamber. The aspirating the second fluid from the second chamber can occur at a location within the second chamber that is different than the location at which the first fluid is aspirated from the first chamber within the respective central regions of the first and second chambers. The aspirating the second fluid from the second chamber can occur at a location within the second chamber that is substantially opposite the location at which the first fluid is aspirated from the first chamber with respect to a central region of the cartridge.

Various aspects of the systems and methods described herein can have one or more of the following advantages.

In some aspects, the systems and methods herein provide for rapid antimicrobial susceptibility testing (AST) and determination of minimum inhibitory concentrations (MICs) for antimicrobial panels. These MICs, along with the microorganism species and antimicrobial, are used to determine the Clinical & Laboratory Standards Institute (CLSI) breakpoint interpretation to provide the clinical AST result for each combination of microorganism species and antimicrobial. Such results take the form of Susceptible (S), Intermediate (I) or Resistant (R) per CLSI publication M-100S. For certain antibiotics, Not Susceptible (NS), and No Interpretation (NI) may be used.

According to CLSI Microbiology standards, an MIC of a given antimicrobial for a given species and strain of a microorganism is defined as the lowest concentration of the antimicrobial in two-fold dilution series that inhibits growth of the microorganism. According to the CLSI manuals and the FDA guidance document for Automated AST systems, a typically preferred standard for this procedure is performed manually, after 16-20 hours of incubation of a 96 well round bottom microwell plate cartridge, and after inoculation with a sample in Muller-Hinton broth. Cartridges meeting standard microplate dimension requirements can be advantageous for handling. The reading can be done manually (e.g., by eye) by a skilled technician. This procedure is very cumbersome, often expensive, and typically requires a lot of hands on technician time and operational planning. Several automated systems have been introduced over the past 30 years. Many automated systems speed the determination of microorganism growth through the use of optical probes. Though these systems may speed growth determination, they are often not capable of providing accurate AST results within the 5-hour "same-shift" cutoff desired or required by microbiology laboratories. In such systems, an algorithm determines the MIC after a sufficient amount of information is collected (e.g., relating to growth amount, rate, etc.) such that the algorithm may decide the MIC with a high confidence level. Because of this, results are not reported at a deterministic (e.g., a pre-defined) time but rather scattered throughout a 24-hour period. Inability to deliver AST results on a consistent schedule and within the same work shift (e.g., for a doctor or a nurse), often delays the delivery of targeted antimicrobial therapies, slows recovery and may, in some cases, increase mortality.

The systems and methods described herein address and reduce some of the drawbacks discussed above with respect to prior systems by separating the process into two or more steps. For example, first, a preliminary testing sequence (e.g., a checkpoint assay) is run for a period of time (e.g., 2-4 hours) after incubation starts. If growth measured during the checkpoint assay is found to be sufficient, the system can start the analysis sequence (e.g., the end point assays (e.g., the final growth/viability assays (e.g., an amplification assay))). If growth measured during the checkpoint assay is not found to be sufficient, the system can incubate for an additional time period (e.g., 8 hours) since slow growing organism are detected (i.e., due to the lack of sufficient growth per the checkpoint assay) and could utilize the additional growth time before the end point assay is performed. Such slow growing organisms are expected to account for less than 5% of all cases tested. Alternatively, the systems can be programmed to interrogate growth in control wells periodically until sufficient growth is achieved for initiation of the end point assay.

BRIEF DESCRIPTION OF THE DRAWINGS

FIG. 5A is a perspective view of an example liquid handling system. FIG. 5B is a perspective view of an underside of the liquid handling system illustrating two sets of fluid handling components. FIG. 5C is a side schematic view of an aspiration nozzle being disposed at an opposite side of a well from a microorganism pellet.

FIGS. 7A-7C are perspective views depicting a cover being closed over cartridges.

DETAILED DESCRIPTION

Figure 1A:
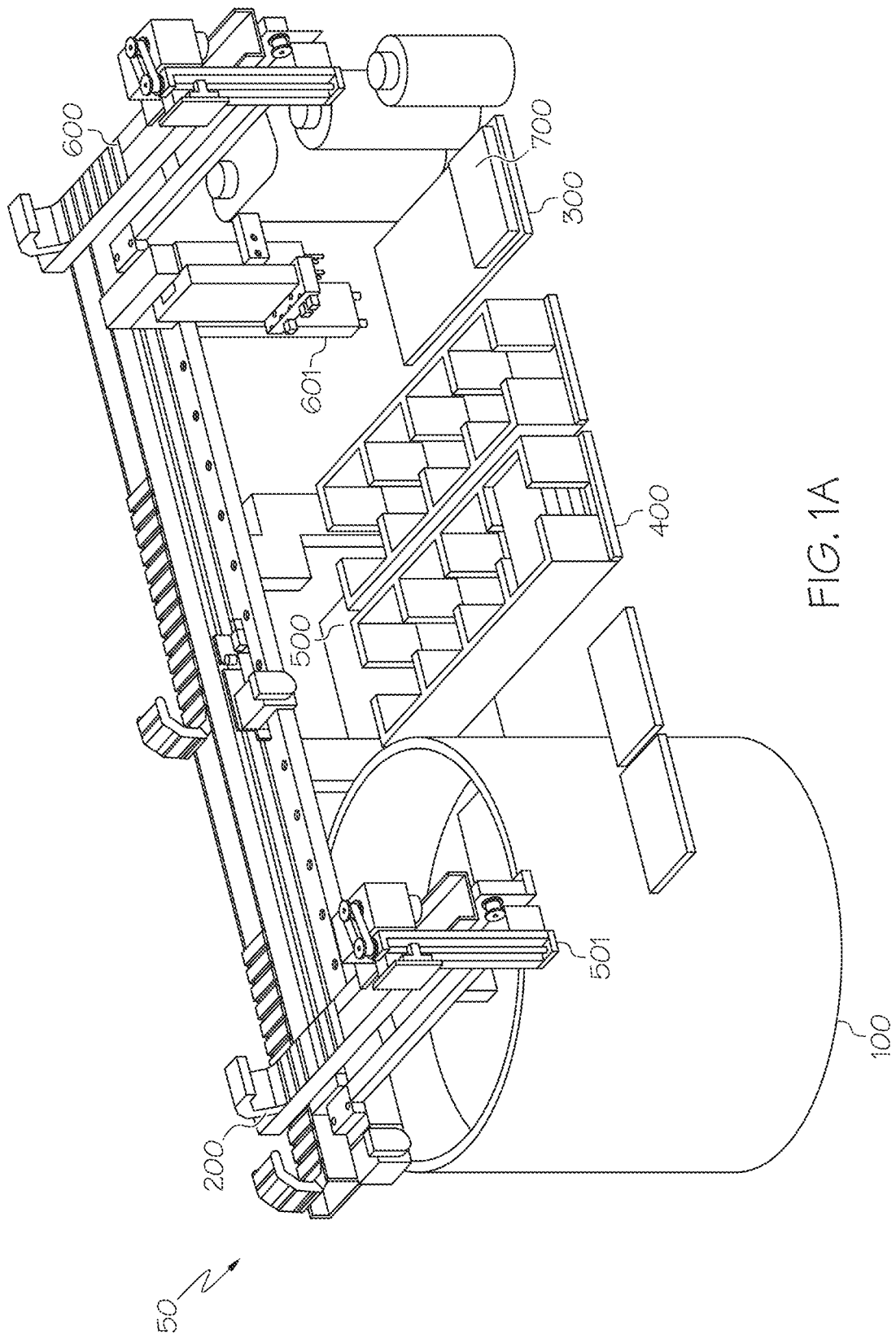
FIG. 1A is a perspective view of an example antimicrobial susceptibility testing system, which can have a centrifuge system to remove excess fluids from test wells.

In some aspects, the systems and methods described herein can relate to automated rapid antimicrobial susceptibility testing systems for performing multi-assay testing sequence, where the testing systems can be configured to at least: receive a loaded test panel; move the loaded test panel to an incubation assembly; incubate and agitate an inoculated sample within the test panel in the incubation assembly; at least once, periodically measure an amount of sample growth in a plurality of control wells of the test panel; responsive to determining that a level of growth in the control wells meets or exceeds a threshold level of growth, stop incubation; perform one or more end point assays on incubated samples in the test panel; measure an optical output from the sample in the plurality of wells of the test panel, the optical output corresponding to an amount of the microorganism remaining in each of the plurality of wells; and report at least one of: a minimum inhibitory concentration of and/or a qualitative susceptibility interpretation for the microorganism remaining in each of the plurality of wells and the plurality of antimicrobials.

For example, in some embodiments, samples to be tested can be inoculated into a test panel (e.g., a cartridge (e.g., a test tray (e.g., a well plate (e.g., a microwell plate (e.g., a 96 or 384 microwell plate (e.g., microtiter plate)))))). In some cases, the cartridges are loaded into the system and can then be handled substantially automatically without human interaction (e.g., using robotics) until the end of the process. Process results can be reported, for example, on a display screen and communicated to a laboratory information management system (LIMS). Additionally, each cartridge can be uniquely defined by a barcode or other unique marking (e.g., laser engraving, direct part marking, RFID, or other marking/identification) that can be scanned either by a user prior to loading or automatically by the system to identify the cartridge and samples to be tested therein.

In some embodiments, cartridges can include a plurality of test cartridge chambers (e.g., wells), each containing a liquid or dried form of an antimicrobial. In some cases, each well can contain a different antimicrobial type and/or concentration. In some cases, the cartridge can have the dried antimicrobials in the wells before the cartridge is loaded into the system. In some cases, the cartridge can have antimicrobials suspended in a medium (e.g., a fluid, such as nutrient broth, e.g., Mueller Hinton Broth). In some cases, the cartridge can have antimicrobials in the form of an antimicrobial film. In some cases, the cartridge can have antimicrobials in solid form. The cartridge can be inoculated with a sample containing microorganisms and loaded into the rapid AST diagnostic apparatus. The microorganisms described herein can be derived from biological samples. In some embodiments, the biological sample is derived from a clinical sample (e.g., which can originate from a patient sample). Example biological samples can include whole blood, plasma, serum, sputum, urine, stool, white blood cells, red blood cells, buffy coat, tears, mucus, saliva, semen, vaginal fluids, lymphatic fluid, amniotic fluid, spinal or cerebrospinal fluid, peritoneal effusions, pleural effusions, exudates, punctates, epithelial smears, biopsies, bone marrow samples, fluids from cysts or abscesses, synovial fluid, vitreous or aqueous humor, eye washes or aspirates, bronchoalveolar lavage, bronchial lavage, or pulmonary lavage, lung aspirates, and organs and tissues, including but not limited to, liver, spleen, kidney, lung, intestine, brain, heart, muscle, pancreas, and the like, swabs (including, without limitation, wound swabs, buccal swabs, throat swabs, nasal swabs, vaginal swabs, urethral swabs, cervical swabs, rectal swabs, lesion swabs, abscess swabs, nasopharyngeal swabs, and the like), and any combination thereof. Also included are bacteria cultures or bacteria isolates, fungal cultures or fungal isolates. In some cases, one or more dilution, isolation, and/or culturing steps can be performed prior to microorganism inoculation.

In some embodiments, prior to loading the automated AST system, the cartridge can be preheated to a temperature that corresponds to the desired temperature of incubation. Preheating can be useful in some cases since standard air convection incubators typically take 30 to 60 minutes to bring a test panel to a desired working temperature. Preheating can be particularly useful for use with the systems and methods described herein for performing rapid AST since typical desired incubation times are below 8 hours and in most cases less than 7 hours, less than 6 hours, less than 5 hours, less than 4 hours, or less than 3 hours. In some embodiments, the incubation of the microorganisms in the presence of the one or more antimicrobials occurs within 30 minutes after preheating the cartridge.

In some embodiments, the plurality of liquid in the cartridge can be preheated to a temperature that is from about 30° C. to about 45° C. In some cases, the preheating can substantially uniformly heat the wells of the cartridge. In some embodiments, the substantially uniform heating of the wells can include heating the cartridge so that a percent different of temperature between a highest-temperature well on a cartridge and a lowest-temperature well on the cartridge that is less than about 5%. That is, in some embodiments, a variation of temperature across the cartridge (e.g., from well to well) is less than about 5%. In some cases, the cartridge is preheated by an addition of at least one fluid at a temperature of at least about 25° C. to the cartridge.

In some embodiments, the cartridge can be preheated for less than about 15 minutes. In some cases, the cartridge is preheated for about 1 minute, about 2 minutes, about 5 minutes, about 10 minutes, or about 15 minutes. In some embodiments, the cartridge is preheated by at least one of radiative heating, conduction heating, and/or convection heating. For example, radiative heating can include infrared radiative heating. In some examples, the cartridge can be preheated by conduction and convection heating. For example, at least one heating surface can perform the conduction and convection heating. In some embodiments, the cartridge can be preheated by both radiative heating and conduction and convection heating. In some embodiments, the cartridge is not preheated by convection heating alone.

In some embodiments, the systems and methods herein provide for automation of a rapid AST, from an inoculated cartridge loading by a technician to a result (e.g., minimum inhibitory concentration and CLSI breakpoint interpretation). In some cases, the cartridge is loaded by a technician and organism identification (ID) information (e.g., species), such as *Staphylococcus aureus*, can be entered or can be obtained automatically by the system's software interface. In this way, ID information obtained using other methods such as mass spectrometry (e.g., MALDI-TOF) or multiplex polymerase chain reaction (PCR) testing can be utilized. In some cases, a cartridge with colorimetric and fluorometric dyes can be used for microorganism ID, known to those skilled in the art as biochemical testing.

In some embodiments, the systems described herein can incubate cartridges and, after a defined period of time (e.g., at least 2 hours) after a cartridge is loaded into the system, interrogate growth check wells at a single timepoint or periodically to perform the checkpoint assay. Once sufficient growth of the sample in the growth check well is detected, the systems described herein can initiate end point assays. The checkpoint assay typically involves direct (e.g., absorbance, nephelometry) or indirect optical measurements (e.g., florescence readout of a metabolic dye) of growth (using a microorganism in nutrient broth), no growth (using nutrient broth without microorganisms therein), and FIT control (measuring the growth or no growth control wells relative to another control well with microorganisms in non-nutritive media such as saline). Indirect measurements can include fluorometric measurements of wells where a reporter can be a redox dye that is converted into a fluorescent form via microorganism metabolism (e.g., resazurin). In such cases, the more microorganisms that are present in a well, the larger the amount of dye converted to fluorescent form, and thus a higher level of fluorescence is measured. That is, the more microorganisms that are present in a well, the faster the conversion to fluorescent form resulting in higher concentration of fluorescent product, and thus a higher level of fluorescence can be measured. In some embodiments, pH sensitive dyes (e.g., phenol red) can be utilized.

Upon determining sufficient growth of the sample in the growth well, the systems and methods described herein can initiate one or more end point assays. The end point assays can include one or more liquid handling, sample separation (e.g., centrifugation, magnetic separation, or vacuum filtration), and aspiration steps during which an amplifier is bound to the surface of the microorganism, unbound reagent can be washed away, and finally an optical signal can be measured and correlated to antimicrobial dilutions and MIC and/or QSR can be determined. Multiple endpoint assays can be performed in the same wells and/or in different wells. Multiple endpoint assays may be advantageous for obtaining accurate MIC and/or QSR data.

In a final step, a time gated luminescence (e.g., time resolved fluorescence) can be utilized to measure an optical signal from the amplifier. In some cases, methods can allow excitation of an amplifier molecule and detection of emitted light, which can be separated both temporally (e.g., detection can be delayed and occurs after excitation when all auto fluorescence has died out) and spectrally (e.g., wavelength of excitation can be more than 100 nanometers (nm) apart from emission which allows usage of less expensive band pass filters). In some embodiments, amplification can be achieved by the addition of a substrate that is catalytically modified by the bound molecule and optical output can be measured. This optical signal can include absorbance signals, fluorescence signals, and/or chemiluminescence signals. In some embodiments, the signal can include electrochemiluminescence (ECL). In some embodiments, upconverting nanoparticles can be used as reporter molecules.

Endpoint assays that may be performed by the system include, but are not limited to, the following: a metabolic assay, a surface-binding probe assay, a chemical probe assay, a biochemical probe assay, an ATP assay, a nucleic acid probe assay, a double-stranded nucleic acid probe assay, an optical density assay, a visual assay, and a pH molecular probe assay.

Figure 1B:
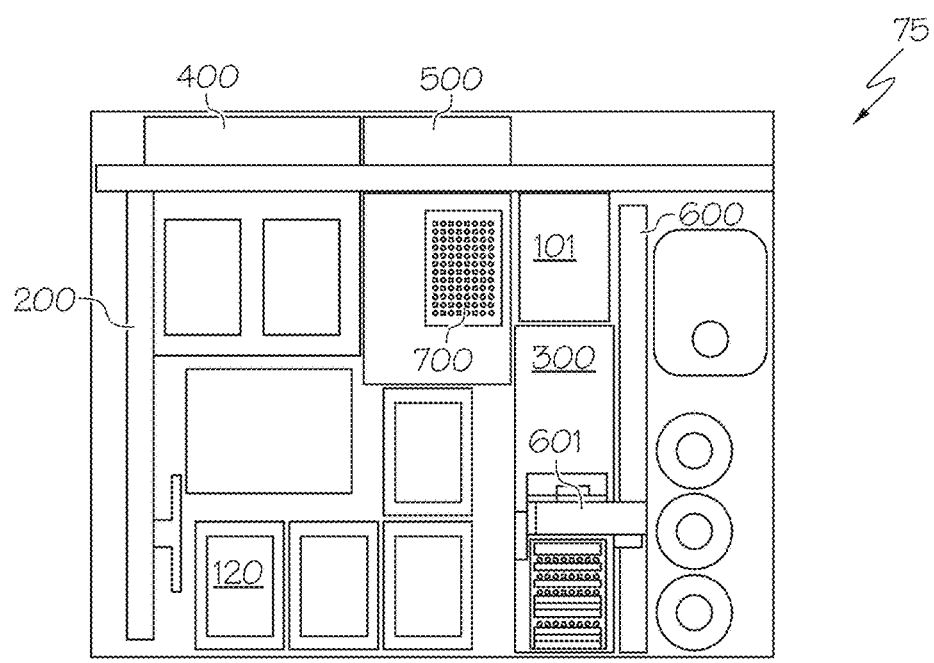
FIG. 1B is a top view of an example antimicrobial susceptibility testing system, which can have a magnetic capture system to remove excess fluids from test wells.

FIGS. 1A and 1B illustrate two example testing systems for performing the antimicrobial susceptibility testing sequences described herein. As described below, both systems are configured to be compatible with cartridges and can typically support 96-microwell plate cartridge and 384-microwell plate cartridge configurations. The example of FIG. 1A illustrates a testing system 50 having a separation system that uses a centrifuge 100. Whereas, the example of FIG. 1B, as discussed below, illustrates a testing system 75 having a separation system 101 that uses magnetics to separate a sample into desired components for analysis.

The testing systems can typically be configured to operate on 120/240V 50/60 Hz AC power. The size and shape of the testing systems can vary based on the specific components disposed therein and the environment in which it will be used. For example, in some embodiments, the testing system can be less than 1 m$^3$ in volume (e.g., in total volume including any external fluid reservoirs). In some embodiments, the testing systems can have a footprint that is less than about 1.0 m$^2$ (e.g., a footprint that is less than 1.0 m$^2$ including any external fluid reservoirs).

The testing systems can be configured to operate under a variety of operating and storage conditions. The testing systems can be configured to operate over a range of about 15 degree Celsius to about 35 degree Celsius. The testing systems can be configured to operate over an environmental pressure range of about 80 to about 110 kPa. The testing systems can be configured to operate over the range of about 25% to about 85% relative humidity, non-condensing. The testing systems can be configured to be rated for operation at altitudes up to about 2,000 m above sea level. The testing systems can be configured to have a dust and moisture ingress protection rating of IP 20. For example, this can limit access to hazardous portions of the device by finger-sized objects and larger.

The testing systems are configured such that, once loaded, the cartridges are moved throughout the systems automatically with little or no operator handling required. This can increase throughput while reducing labor time and errors. For example, the system 50 can include a robotic transfer system (e.g., a 3-axis robotic arm) 200 with a gripper and light collection subassembly 501. The gripper can be used to expose (e.g., de-lid) cartridges and move the cartridges between the subassemblies within the system for processing a sample. The light collection subassembly 501 can include or otherwise be connected to an optical network (e.g., fiber optics), which can be used to carry one or more optical signals (e.g., light) from light collection subassembly 501 to an optical readout subsystem 500. In some embodiments, light collection from the sample being tested, readout, and measurement can be integrated in and processed with a single subsystem that is serviced by the robotic arm 200. The subsystem can include an x-y motion stage to move the cartridges and/or optical system to address each well of the test panel within the cartridges.

A loading device (e.g., drawer) 300 can be used for loading cartridges (e.g., cartridges 700, 701) into the system. Once loaded, the robotic transfer system 200 can move the cartridges to the incubation subassembly 400 to begin processing. The incubation subassembly 400 is configured to provide controlled heating and shaking of the samples and cartridges to perform the various assays. In some embodiments, the incubation subassembly 400 can include a humidity control system configured to control or modify the humidity of the air surrounding the samples.

The optical collection subsystem 501 can be configured to periodically perform one or more check point assays, which can include checking control wells and determining whether sufficient growth is achieved in order to initiate the end point assay. Once the end point assay is initiated, plates can be transferred to a liquid handling subassembly 601 by a robotic system 600. Alternatively, liquid handling can be performed at another location within the testing system 50, including within other subassemblies, such as within the separation system (e.g., centrifugation system) or the incubation subassembly. The liquid handling subassembly 601 can also perform aspiration, washing, and solution addition to and from the individual wells in the cartridge. For example, when a cartridge is centrifuged, the resulting pellets of microorganisms may not distribute uniformly in every well of the plate. For example, this could be caused by a planar cartridge being placed tangent to the centrifuge's rotational radius and parallel to its axis of rotation. Such placement combined with the centrifugal force generated by the orbital motion may distribute the pellets nonuniformly throughout the cartridge wells. In some cases, the centrifugation may distribute pellets to an outermost position with respect to the center of orbit of the shaking motion. In some cases, certain types of cartridges, such as plates with wells having U-shaped or V-shaped bottoms, may resist such radial spreading of the pellet during centrifugation better than a well having a flat bottom. As such, it is typically beneficial for the aspiration to account for the varying pellet position by placing the aspiration nozzle away from the pellet in each cartridge well. FIG. 5C depicts an example aspiration nozzle 604 disposed opposite a pellet.

Thus, fluid can be aspirated from different locations or regions within each cartridge well based on the expected positions of the pellet. In some cases, pellets along a left side of a cartridge may get distributed toward a left side of each of the individual wells (e.g., at 6 o'clock to 12 o'clock positions (e.g., at 9 o'clock to 12 o'clock positions)), and pellets along a right side of the cartridge may get distributed toward a right side of each of the individual wells (e.g., at 12 o'clock to 6 o'clock positions (e.g., at 12 o'clock to 3 o'clock positions)). Therefore, fluid can be aspirated from the wells along the left side of the cartridge at an opposite position along the right side of the well (e.g., at 12 o'clock to 6 o'clock positions (e.g., at 3 o'clock to 6 o'clock positions)) and fluid can be aspirated from the wells along the right side of the cartridge at an opposite position along the left side of the well (e.g., at 6 o'clock to 12 o'clock positions (e.g., at 6 o'clock to 9 o'clock positions)). Of course, the specific locations or regions here are provided as examples and other configurations are possible.

The centrifugation subassembly 100 is configured to separate microorganisms (e.g., microorganisms of a microbial origin, (e.g., a bacterium, a fungal cell, an archaeon, and a protozoan)) within the sample from other fluid or components within the well. For example, the centrifugation can pellet microorganisms within the sample based on density gradient and can be used to separate microorganism with bound amplification reporter molecules from unbound molecules comprising growth nutrient broth or metabolic dye reporter molecules.

FIG. 1B shows another example embodiment of a testing system 75, which includes apparatus using a magnetic capture separation system 101. The magnetic separation system 101 can include a stand 110 with magnetic separation device 111 disposed thereon. In some cases, the stand 110 can include a shaking subsystem 112 that imparts orbital or axial agitation on a cartridge positioned on the stand 110. The magnetic capture stand 110 can include one or more magnetic field generating components to generate a magnetic field within a sample disposed thereon. For example, the magnetic capture stand 110 can include a two-dimensional array of magnetic elements 1110 in a configuration that corresponds to the wells of the cartridge. In some embodiments, the magnetic elements 1110 can be substantially evenly distributed across the stand to mate with the test panels when they are disposed within the stand. For example, 96 (or another number corresponding to a number of wells in a cartridge) magnetic elements (e.g., magnets (e.g., cylindrical magnets)) can each be placed beneath a well of a 96-well cartridge, 24 cylindrical magnets placed in the interstitial space between the wells of a 96-well cartridge, 96 open-cylinder shaped magnets each placed beneath a well of a 96-well cartridge to capture magnetic material in a ring-shaped pattern about the well center. Similar distributions of magnetic elements can be used for 384-well cartridges but with 384 magnetic elements.

In some examples, the magnetic separation device 111 can be configured to be retractable, for example, to vary or remove the magnetic field being applied to the samples in the test panel, to allow liquid handling and re-suspension of magnetic particles in situ. In some examples, the magnetic stand 110 can be coupled to (e.g., substantially fixed upon) an orbital or axial shaker station 112. For example, orbital shakers can include an off-centered rotating component (e.g., an eccentric cam system). Orbital shakers can also be formed by multiple axial actuators (e.g., an x-y table). In some cases, additional shaker stations can be included to incubate reaction and increase binding rate of end point assay reactions via agitation. Unless stated, the testing system 75 can include one or more other components or features of the testing system 50 described herein.

Figure 2A:
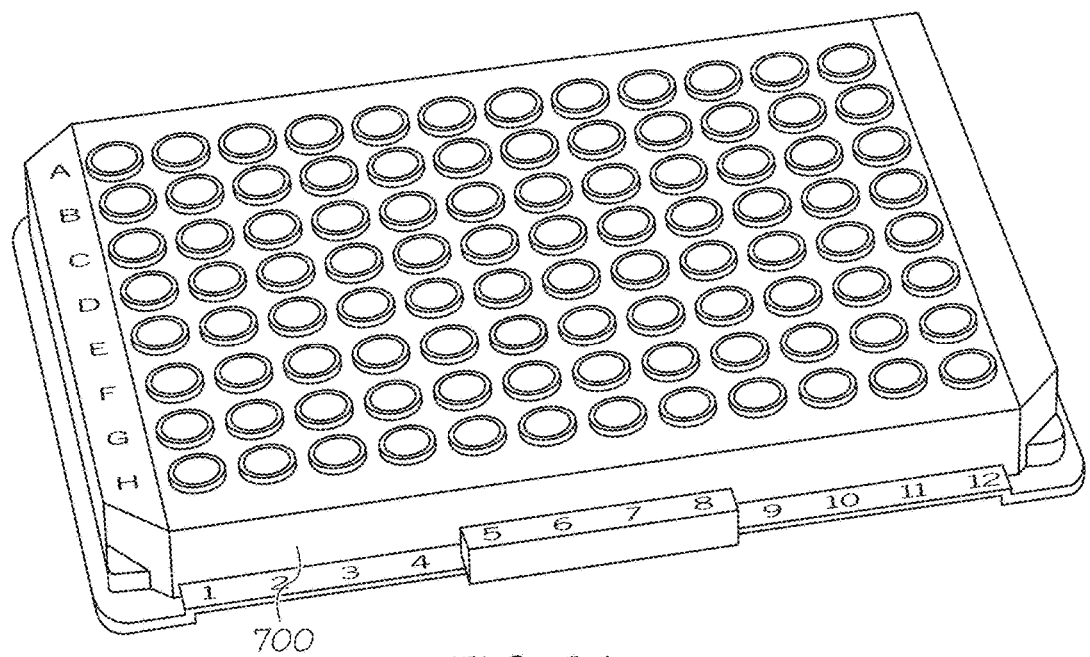
FIG. 2A is a perspective view of an example cartridge, for example, having 96 test wells.
Figure 2B:
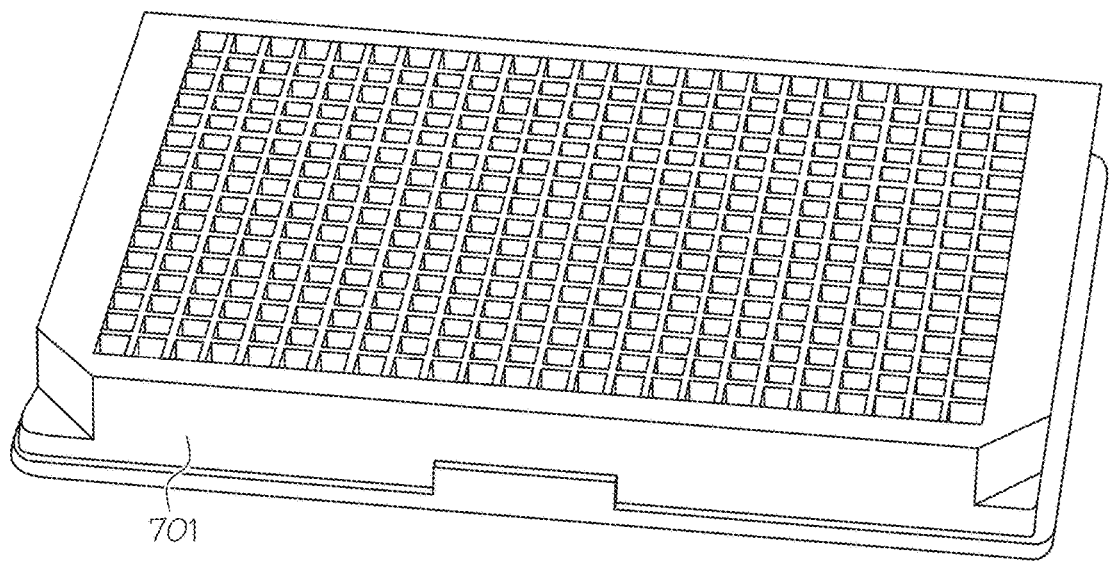
FIG. 2B is a perspective view of an example cartridge, for example, having 384 test wells.

FIGS. 2A and 2B illustrate example cartridges that can be used with the testing systems 50, 75 described herein. For example, FIG. 2A represents an example 96-well plate 700 that defines 96 individual vessels (e.g., chambers (e.g., wells)) that can each contain and sample and undergo testing. In some cases, the plate can be a standard ANSI 96-well plate cartridges. Additionally, FIG. 2B represents an example 384-well plate cartridge 701 that defines 384 individual vessels (e.g., chambers (e.g., wells)) that can each contain a sample for undergoing testing. In some cases, the plate can be a standard ANSI 384-well plate. In some embodiments, the well plate cartridges can include flat-bottom cartridges, V-bottom cartridges, and/or U-bottom cartridges. In some cases, the cartridges can be made of polystyrene, which can be clear or opaque. While 96-well and 384-well cartridges are primarily discussed herein, other examples are possible. For example, the cartridge can include any number of wells, such as at least 2, 4, 6, 8, 12, 24, 48, 96, 192, 384, 1536 or more wells.

Figure 18:
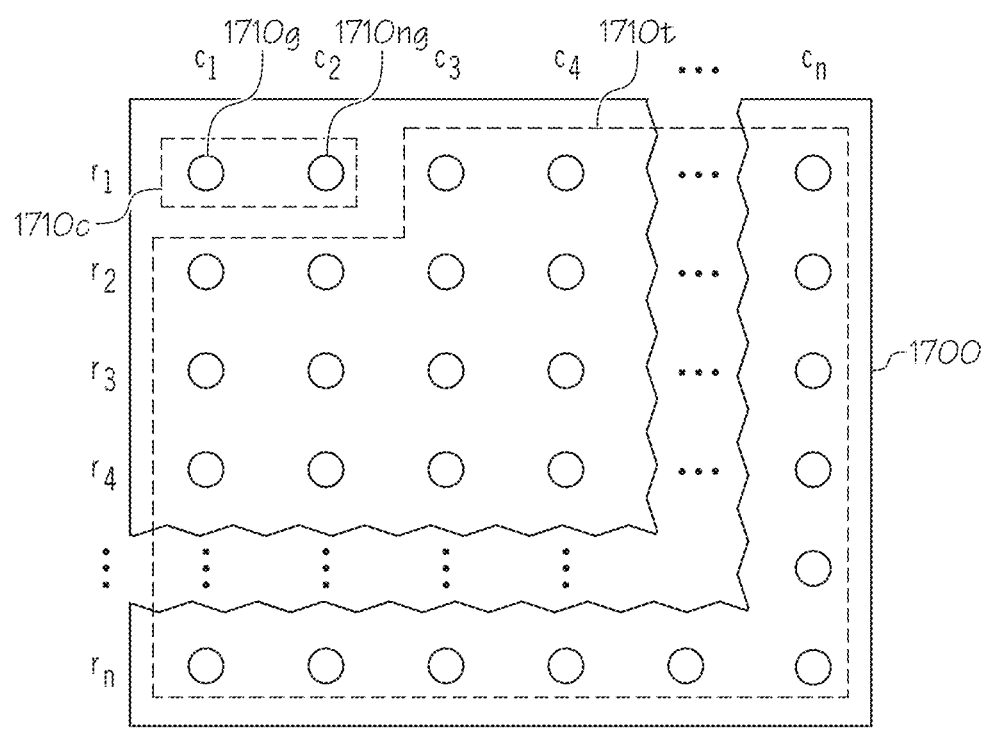
FIG. 18 is a schematic view of a cartridge depicting an example configuration of wells for performing a check point assay and one or more endpoint assays.

As described herein, cartridges can be used to contain various combinations of fluids in order to carry out multiple testing sequences, such as a check point assay, metabolic assay and one or more end point assays. In some cases, a cartridge can have a set of wells used to facilitate the check point assay and a set of wells used to facilitate the end point assays. By way of example, in some embodiments, referring briefly to FIG. 18, a cartridge 1700 can include an array of wells arranged in rows and columns. The cartridge 1700 can include a set of control wells 1710c and a set of antimicrobial testing wells 1710t. In the example of FIG. 18, the set of control wells 1710c includes two wells and the set of testing wells 1710t can include the remainder of wells along the plate. In some embodiments, the set of control wells 1710c can include at least two wells, where one well is a growth well 1710g and another well is a no-growth well 1710ng. As discussed in detail below, in some embodiments, the growth well can include, or be inoculated to include, a combination of broth and a sample such that the microorganisms in the sample can grow within the broth during an incubation period. Typically, antimicrobials are not added to the growth well. Whereas, in some embodiments, the no-growth well 1710ng can include, or be inoculated to include, broth without the sample (i.e., broth in the absence of the microorganisms from the sample). Typically, antimicrobials are also not added to the no-growth well. Thus, during an incubation period, the no-growth well can serve as a baseline as compared to the growth well in which the microorganisms can grow.

The testing wells 1710t can include any of various combinations of the sample and various types and concentrations of antimicrobials for which susceptibility can be analyzed. In some cases, rows of wells can be dedicated to a particular antimicrobials and concentration of that antimicrobial can vary between columns. For example, a cartridge can have row of wells containing penicillin where each well from left to right contains an increasing concentration of penicillin.

Of course, other examples are possible. For example, the different wells and sets of wells can be positioned at any of various locations along a cartridge. Additionally, the different sets of wells (e.g., control wells and testing wells) can include greater or fewer individual wells along the cartridge. Additionally, in some cases, not all wells are used/occupied during testing.

An antimicrobial dilution series can be frozen, dried, or prepared fresh prior to plate inoculation with a sample. In some cases, inoculation of cartridges can be performed either by hand or using an automated system. In some examples, such as in cases of fresh antimicrobial plates, an automated liquid handling system can be used to prepare the cartridge with antimicrobial dilution series. Inoculation processes can include any of various processes that may be conventional in the art.

Consumable Components

Figure 3:
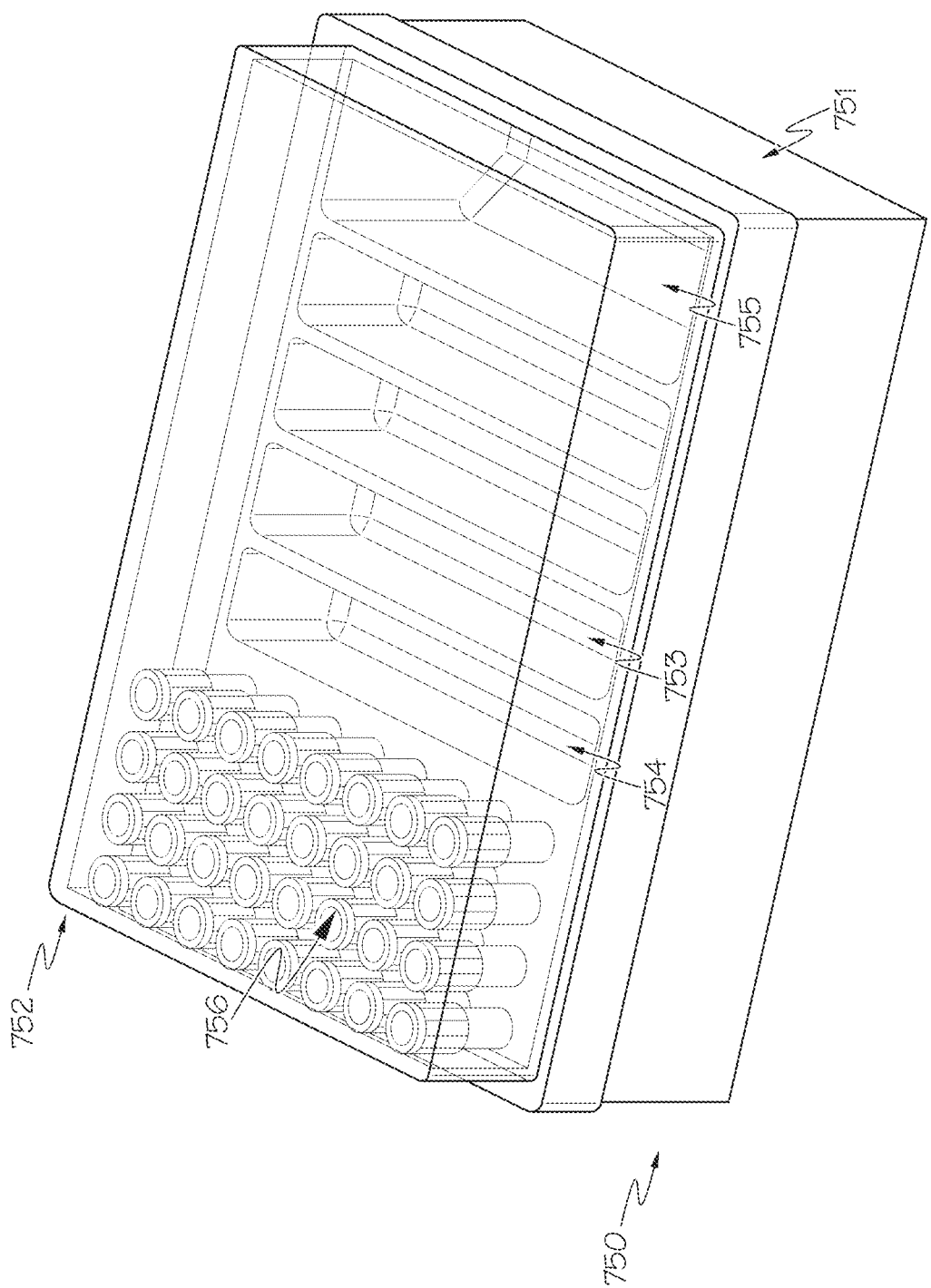
FIG. 3 is a perspective view of an example consumable assembly tray, housing disposable tips and reagents.

As depicted in FIG. 3, one or more reagents used for liquid processing within the system 50 can be stored within a consumable tray 750. The consumable 750 typically includes a tray 751 and a cover 752. The inside of the consumable can be sealed with a sealing layer (e.g., foil) 753 that protects its contents from the environments, such as from moisture, from light, and from evaporation. The foil 753 can be pierced by the liquid handling system or removed by the user. The tray 751 includes one or more reagent troughs 754, one or more wash troughs 755, and one or more pipette tip holders 756. The consumable 750 can be configured to provide an adequate amount (e.g., volume) of the fluids and other consumables (e.g., pipette tips/nozzles) required to run multiple testing sequences. In some embodiments, the consumable 750 can include enough reagents and consumables sufficient for at least 10 (e.g., at least about 20-100) cartridges per day per system. In some embodiments, reagents can additionally or alternatively be stored in bottles in larger volumes. Both the consumables 750 and/or bottles to hold reagents can be refrigerated. In some cases, refrigeration can be performed within the testing system. In some cases, each newly loaded reagent consumable 750 or bottle can include identifying information (e.g., a barcode) that is read (e.g., scanned) prior to or during the loading into the system. In some examples, the system can notify a user (e.g., operator) if a consumable is empty (i.e., lacks a sufficient volume of a reagent to perform a testing sequence) or contents are expired. In such cases, the system can prompt the user to load a new consumable 750.

The consumable 750 can be designed and configured to withstand storage throughout a range of temperatures (e.g., between about 0° C. and about 10° C. (e.g., about 4° C. nominal)) for a shelf life time period (e.g., up to about 6 months) without substantially affecting assay performance. In some embodiments, the consumable can provide sufficient protection from light (e.g., to block light from entering the consumable). For example, in some cases, the consumable can be opaque. This can help preserve some reagents that are light sensitive and can degrade when exposed to light for long periods of time. In some embodiments, the consumable can be usable in a 35° C. environment for up to about 12 hours without substantially affecting assay performance. In some cases, the 12 hours can accommodate a typical 10-hour shift with 2 hours of margin.

Figure 4:
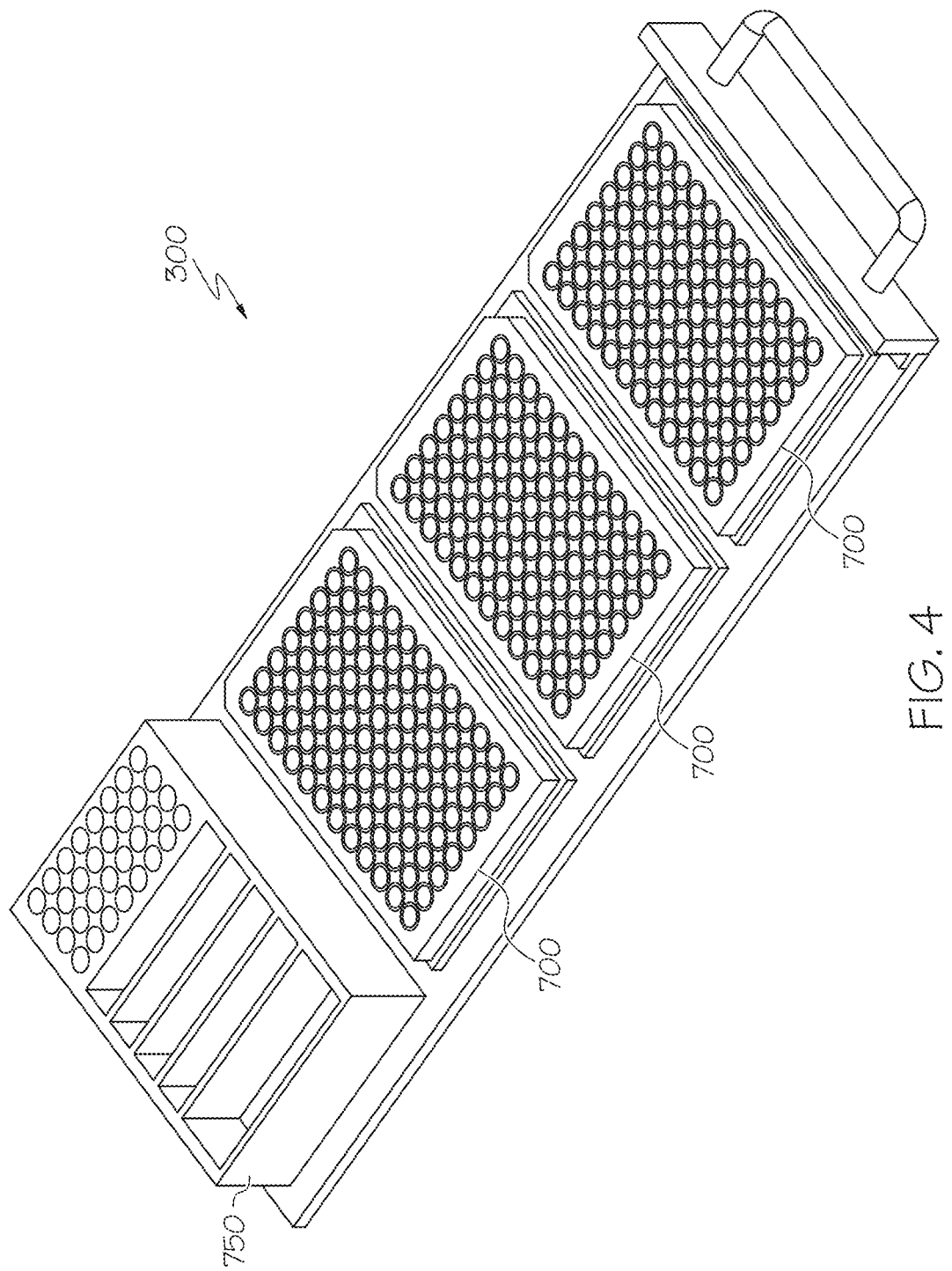
FIG. 4 is a perspective view of an example loading assembly, facilitating loading cartridges and consumable assembly trays.

In some embodiments, such as in the example illustrated in FIG. 4, the loading drawer 300 can be used to load cartridges 700 and/or the consumable tray 750 into the system. Once loaded, the robotic system 200 moves plates 700 between the various subsystems. In cases where a reagent consumable tray 750 is used, the consumable 750 can be loaded onto a drawer 300 along with the cartridges 700 and moved by robotic gripper to appropriate place within the system. In some examples, the consumable 750 is configured to be sized (e.g., have a foot print) that is substantially similar to the cartridges 700, which can simplify loading and unloading systems, as well as robotic gripper systems.

Fluid Handling Systems

Referring to FIGS. 5A and 5B, the testing systems can include a fluid processing assembly 601 having various components that can be individually or in combination to deliver and withdraw fluids to and from the cartridges. In some embodiments, the fluid processing assembly is mounted on a separate multi axis robotic system 600 (shown in FIGS. 1A and 1B) and include reagent delivery components (e.g., nozzles) 602, sample wash components (e.g., nozzles) 603, and sample aspiration components (e.g., nozzles) 604. The fluid handling components and nozzles can include pipette devices (e.g., single and/or multichannel pipette heads) or any of various other types of manifolds. In some embodiments, the fluid processing assembly includes discrete (e.g., non-multiplexed) fluid pathways for each dispensed liquid (e.g., reagents, wash buffer, etc.) with 4 dedicated to reagents and 3 dedicated to buffers.

For each reagent and buffer fluids displacement, the fluid processing assembly 601 is configured to dispense a specific target volume per well in a target maximum time period. For example, for a 96-well cartridge, the fluid can be dispensed in less than about 20 seconds. In some cases, this time period can be defined from the time the liquid begins filling the first well to the time the liquid finishes filling the last well of the cartridge. In some examples, fluid dispensing can be completed in less than approximately 10 seconds using a 5 microliter peristaltic pump cassette with an 8-channel manifold. For a 384-well cartridge the fluid can be dispensed in less than about 80 seconds.

By way of example only, in some embodiments, the fluid processing assembly 601 can dispense the following nominal volumes of each assay liquid uniformly across the cartridge:

| Liquid | Volume (µl) - 96-well microwell plate | Volume (µl) - 384-well microwell plate |
| --- | --- | --- |
| Reagent C | 10 | 5 |
| Reagent A | 10 | 5 |
| Reagent B | 10 | 5 |
| Assay Buffer | 100 | 50 |
| Wash Buffer | 200 | 100 |
| Blast Buffer | 100 | 50 |

Any of various fluid processing tolerances can be achieved. For example, in some embodiments, the fluid processing assembly 601 can, for example, dispense the buffer liquids with accuracy of +/−3% of nominal and precision of 3% coefficient of variation (CV). The fluid processing assembly can also, for example, dispense the reagent liquids with accuracy of +/−2% of nominal and precision of 2.5% CV. The fluid processing assembly can, in some embodiments, dispense reagent and buffer liquids using different dispensing technologies to achieve the accuracy and precision. For example, dispensing can be performed using a multi-channel manifold with one common inlet or a multi-channel fluid-displacement (e.g., air, water, or oil), head (e.g., pipette) with individual channels dispensed in parallel.

The fluid processing assembly 601 can also be configured to not touch the liquid in the cartridge wells with the dispenser nozzles during use. In some embodiments, the system is configured to substantially automatically (e.g., automatically) perform routine cleaning required to prevent clogging or buildup of residues on the dispenser nozzles.

Fluid delivery through the various handling components can be driven by one or more pumping devices (e.g., positive displacement pumps, air displacement pumps, syringe devices, peristaltic pumps, and/or diaphragm pumps). From the pump outlet, the fluids can be dispensed through a manifold consisting of 1 or more fluid inlets (from the pump) and 1 or more fluid outlets (e.g., 1, 8, 12, 16, 96, or 384). Such manifolds, combined with 1 or more pumps (e.g., 1, 2, 8, 12, 16, 96, 384) can dispense fluid into 1 or more (e.g., 1, 8, 12, 16, 96, 384) microplate wells simultaneously or in "strips" (e.g., successive or interleaved microplate rows or columns). Suitable fluidic systems can be manufactured by companies, such as Accel Biotech of Los Gatos, Calif., US; Hamilton Robotics of Reno, Nev., US; Tecan of Maennedorf, Switzerland; or Beckman-Coulter of Brea, Calif., US.

Gripper & Robotic Systems

Cartridge handling, such as moving cartridges between the various subassemblies or covering and uncovering the cartridges for processing, referred to herein as de-lidding, can be done using a robotic handling component, such as a 3-axis robotic gripper. As discussed below, the gripper allows substantially automated loading and unloading to and from centrifuge 100, shaking incubator 400, optical readout 500, and liquid handling 601 subsystems. For faster optical analysis and readout, the components of the optical system can be coupled to the gripper head 501, for example, using fiber optics and appropriate optical elements, to allow better light collection.

Figure 17:
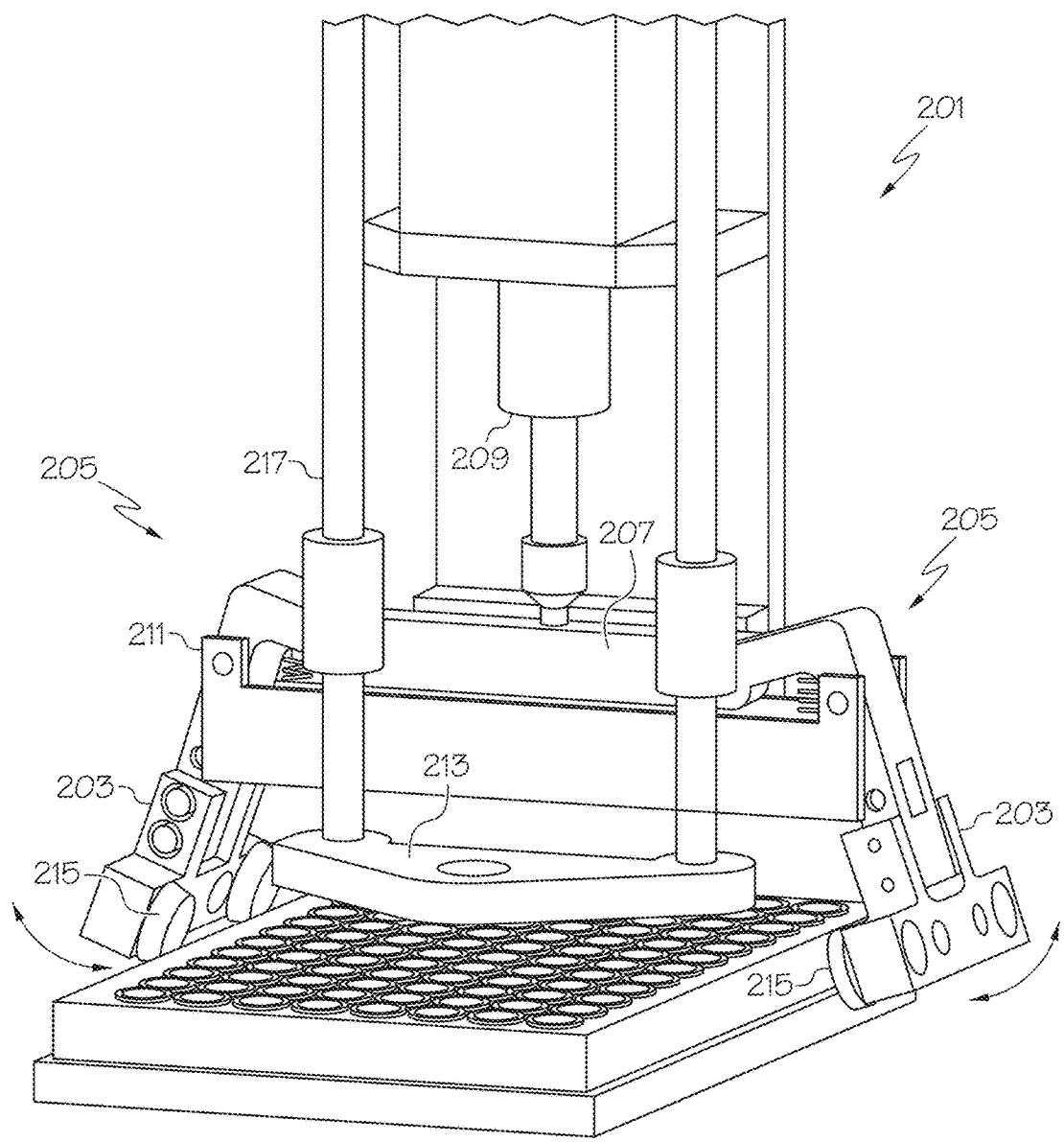
FIG. 17 is a perspective view of a robotic gripper device for handling cartridges and other cartridge handling components of the testing systems.

Referring briefly to FIG. 17, a gripper (e.g., gripping mechanism) 201 can include a pair of gripping components (e.g., angular arms) 203. The arms 203 can be connected by linkages 205 to a transfer bar 207 to articulate the arms. The transfer bar 207 can be driven by a linear actuator (e.g., a stepper motor driving a lead-screw mechanism) 209 to move the free end (e.g., distal ends) of the gripper arms in a closing (e.g., pinching (e.g., clamping)) motion using a pivot 211. For example, in some embodiments, the actuator can pull the transfer bar 207 toward the actuator to pivot the arms 203 about the pivot 211 and close the arms. The actuator can also push the transfer bar 207 away from the actuator to pivot the arms 203 about the pivot 211 to open the arms. Other types of linkage configurations are possible. The closing motion can articulate the arms to place the free ends of the arms in a substantially parallel orientation (e.g., closed or gripped position), allowing the gripper to grab and retain an object. In some embodiments, the arms 203 can include one or more retention elements 215 to help grasp and hold various surfaces of a held component and reduce the likelihood that the held component would slip from the gripper. For example, the retention elements can include a textured or rubber surface (e.g., a rubber foot). In some cases, the position and clamping force of the arms and retention elements can be adjustable.

This gripper mechanism can additionally include systems configured to facilitate vertical (e.g., z-axis) travel either separate from or part of the robotic handling component to which it can be connected. The gripper arms 203 can be passively biased (e.g., using linear spring mechanism (e.g., springs)) to a particular starting position (e.g., open or closed).

The gripper 201 can also include a mounting location 213 for one or more tools or systems. For example, in some examples, the optical systems can be mounted on the mounting location so that the fiber optic optical reader can inspect the wells. The mounting location 213 can be coupled to the gripper 201 using one or more guide rods 217 connected to the gripper or directly to a robotic arm.

Objects to be gripped can include cartridge lids, gripper accessories (e.g., other grippers such as a cartridge lifting device (e.g., the transfer system 1200 and the lifting fingers 1202 discussed below)), or cartridges themselves. In some cases, the gripper arms 203 can be configured to grip and handle a cartridge so that the cartridge can be lowered into a centrifuge system.

Incubation Systems

Incubation of the samples to be tested in a cartridge can be an important aspect of the phenotypic antimicrobial susceptibility testing systems described herein. In some examples, incubator temperatures can be held at a consistent temperature, such as at or less than about 45 degrees Celsius (e.g., less than about 35 degrees Celsius (e.g., about 33 degrees Celsius to about 35 degrees Celsius (e.g., 35 degrees Celsius))). The incubator temperatures can be controlled by heaters, air circulation system, and appropriate air directing features (e.g., ductwork). Heat can be conveyed to the cartridges from these heaters or using a combination of other techniques, such as convection, conduction, radiation, or advection. It is expected that temperatures higher than about 35 degrees Celsius can increase growth speed but can interfere with, or negatively impact, some antimicrobials, such as oxacillin. However, in some embodiments, such as in cases having test panels where these antimicrobials are not present, incubation can be performed at higher temperature. Additionally, other conditions, such as gases and ambient gases present, can be controlled for incubation. For example, in some embodiments, incubation systems are configured to generate desired conditions for incubation that promote microorganism growth, such as ambient air, anaerobic conditions, or up to 10% $CO_2$.

Additionally, agitation of the cartridges and samples therein, such as orbital or axial shaking, can be used during incubation to promote better oxygenation of microorganisms and uniform exposure to nutrients in growth media (e.g., a liquid, solid or semisolid media). Agitation can consist of one or more (e.g., 1, 2, 3, 4, 5, 6) axis linear, orbital (e.g., circular, ellipsoid, etc.), or semi-orbital motions performed periodically with a particular defined duty cycle from 1-100%. In some embodiments, the cartridge is agitated by means of mechanical agitation, acoustic agitation, and/or magnetic agitation. In some cases, the mechanical agitation is orbital shaking. The speed and displacement of agitation can be adjusted (e.g., optimized) specifically optimized for test panel configuration for additional performance. For example, test panels having smaller well sizes (e.g., diameters) such as in 384-well cartridges, can benefit from agitation that is performed with higher frequency and smaller diameter orbit (in the case of orbital agitation) compared with larger wells such as in 96-well cartridges. This change in agitation can be useful to keep the liquid in the cartridge wells smoothly swirling within the well as the plate geometry changes.

It is noted that agitation, as used herein, can refer to generated motion that is generally insufficient to cause what one skilled in the art would understand to be mixing. That is, solution mixing is well understood by those skilled in the art to promote microorganism growth rates in large growth solution volumes (e.g., >10 mL) by enhancing solution aeration. Broth microdilution AST assays are commonly performed in cartridges comprising wells with lateral dimensions <12 mm. For example, in one example, in order to achieve proper mixing in wells with lateral dimensions <12 mm, the orbital shaking frequencies are at least 500 revolutions per minute (rpm). However, these frequencies may inhibit microorganism growth in wells with lateral dimensions <12 mm due to high strain and shears on the microorganisms.

In some embodiments, the methods provide for promoting microorganism growth by agitating the cartridge at a frequency or a radius insufficient to achieve solution mixing. Agitation of the cartridges and samples therein, such as orbital or axial shaking, can be used during incubation to promote better oxygenation of microorganisms and uniform exposure to nutrients in growth media. Surprisingly, it was found that sub-mixing-inducing shaking frequencies and radii enhanced microorganism growth rates.

In some embodiments, agitating the cartridge at a frequency or a radius insufficient to achieve solution mixing can result in a greater growth ratio between microorganism growth with agitation of the cartridge as compared to microorganism growth without agitation of the cartridge.

Figure 6A:
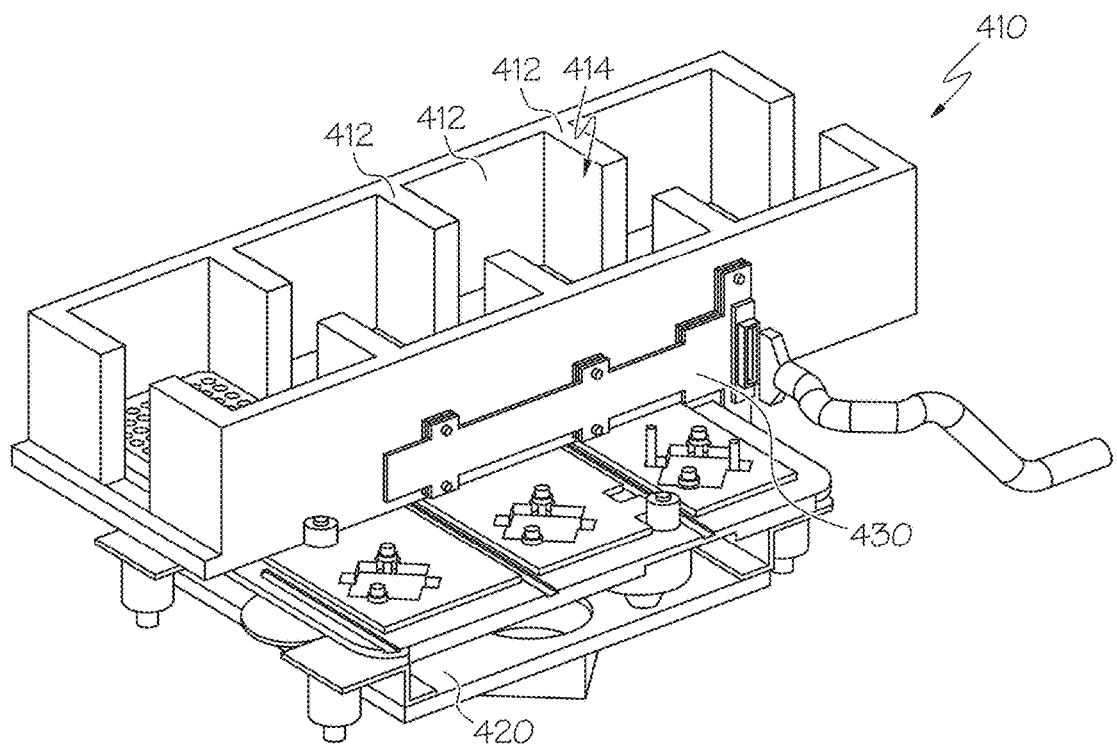
FIG. 6A is a perspective view of a shaking incubation system.
Figure 6B:
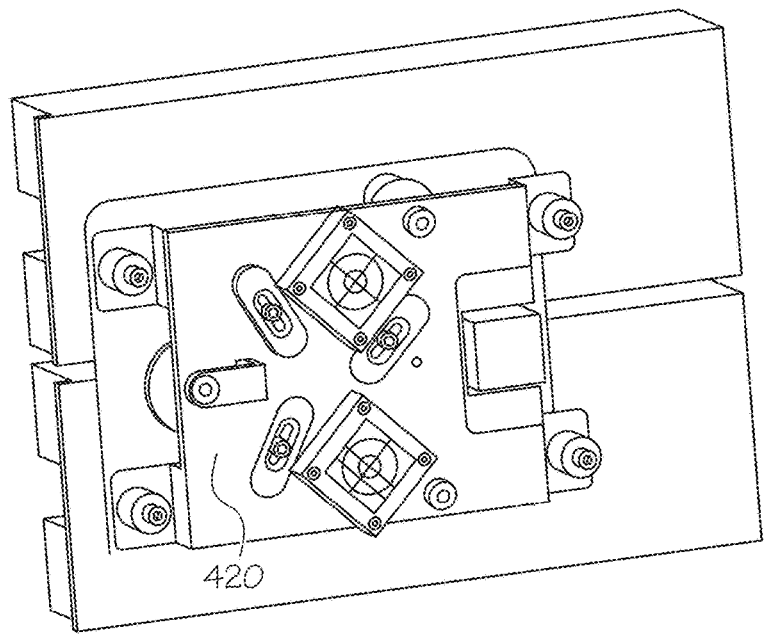
FIG. 6B is a perspective view of an underside of the shaking incubation system, illustrating cartridges supported on a shaking mechanism.

Various incubator designs can be implemented with the testing systems described herein. For example, compact nest style incubator designs, shown in FIGS. 6A and 6B, which allows for a high capacity compact system in which multiple cartridges can be stacked and processed at once. In some embodiments, a nest configuration can include a frame 410 having one or more side walls 412 that form individual cartridge storage chambers (e.g., nests) 414. In some cases, the storage chamber can be configured to have a foot print that corresponds to (e.g., is slightly larger than to accommodate) a cartridge. In some examples, the frame 410 and/or the individual storage chambers 414 can be heated to provide more consistent (e.g., uniform) and faster heating of cartridges disposed therein. In some examples, each nest 414 is sized and configured to accommodate 4 plates stacked on top of each other. However, other numbers of plates can be accommodated depending on nest size. In some embodiments, the incubators can have a capacity of at least 10 cartridges. Cartridges can be stacked with or without separating components (e.g., separators (e.g., thermally conductive separators)) disposed between the cartridges. For example, in some cases, separating components formed of one or more thermally conductive materials can be disposed between cartridges for more uniform and faster heating. In some cases, the systems and methods described herein can yield faster testing and the testing of more cartridges than some conventional systems. For example, in some embodiments, the testing system can yield a throughput of at least 4 cartridges in about an hour, at least 6 cartridges in about an hour, at least 8 cartridges in about an hour, and/or at least 10 cartridges in about an hour. In some embodiments, the testing system can yield a throughput of at least about 50 cartridges per same day shift, and/or at least about 100 cartridges per same day shift.

In some embodiments, cartridges are pre-heated prior to loading into the system, for example, to a temperature that is at or near the working temperature of the incubator. For example, in some cases, pre-heating can be performed rapidly using a thermally conductive material (e.g., metal plate) having surface structure to allow better thermal contact with the plate. In some cases, preheating can be performed using a heater (e.g., an infrared heater, electromagnetic heater (e.g., electromagnetic radiation (e.g., microwaves)). In some embodiments, heating can be performed within the testing system, for example, at loading station.

As discussed above, better (e.g., more rapid and steady) growth during incubation can be achieved by agitating the sample in a manner which enables oxygenation and better distribution of growth media nutrients throughout the cartridge well. Any of various agitation systems can be implemented to impart motion on the samples. For example, in FIGS. 6A and 6B, a driver system 420 can be used to impart an orbital motion to shake the sample in a circular motion. In some cases, the driver system 420 can control orbital speed and radius of the motion of the frame 410. In some cases, the orbital speed and radius can be variable (e.g., adjustable) to achieve a variety of different speeds and radii. Additionally, in some cases, the orbital speed and/or radius can be variable during operation. For example, a radius of the orbital agitation (e.g., orbital radius) of the sample can be less than about 25 mm (e.g., about 1 mm to about 12 mm (e.g., about 1 mm to about 10 mm (e.g., about 1 mm to about 8 mm (e.g., about 1 mm to about 3 mm (e.g., about 2 mm to about 3 mm))))). The driver system 420 can be driven by any of various combinations of motor, belts, gears, cams or other electromechanical components. In some cases, orbital speed and radius of motion can be user adjustable and adjusted (e.g., optimized) for different panel formats and samples to be tested. For example, in some examples, 384-well plates can be agitated along an orbit having a diameter of about 4 millimeters and 96-well plates can be agitated along an orbit having a diameter of about 8 millimeters.

In addition to orbit diameter, orbital rotation speed can also affect microorganism growth rates. For example, the orbital shaking occurs at a frequency of greater than about 50 revolutions per minute. In some examples, the orbital shaking occurs at a frequency of greater than about 350 revolutions per minute (rpm). In some examples, the orbital shaking occurs at a frequency of less than about 750 revolutions per minute. In some examples, the orbital shaking occurs at a frequency of about 150 revolutions per minute. For example, speeds between about 150 rpm and about 650 rpm have been shown to promote acceptable rates of microorganism growth.

In some embodiments, the orbital shaking occurs at a frequency of greater than about 50 revolutions per minute. In some examples, the orbital shaking occurs at a frequency of greater than about 350 revolutions per minute. In some examples, the orbital shaking occurs at a frequency of less than about 750 revolutions per minute. In some examples, the orbital shaking occurs at a frequency of about 150 revolutions per minute. In some embodiments, the radius (e.g., orbital radius) can be greater than about 2 mm. In some embodiments, the radius can be about 25 mm.

In some cases, it may not be necessary for the agitation of the cartridges to be performed continuously throughout the incubation time, but a duty cycle of at least 10% can be beneficial.

The incubator nests 414 can be accessed from a variety of different locations, such as the top or sides. In some cases, referring to FIGS. 7A-7C, an actuator (e.g., linear actuator) 440 can be used to open nests from the top, side, or in clam shell configuration. For example, the actuator 440 can be configured to drive a lid 450 used to cover the cartridges (e.g., enclose cartridges within the storage chambers 414).

Cartridges can also be housed in other configurations. For example, in some embodiments, a multi-level incubator (e.g., multi-floor (e.g., hotel style) incubator) is used. Referring to FIGS. 8A-8D, hotel style incubators 760A, 760B, 760C, 760D can include one or more cartridge holding trays (e.g., floors) 765 by which different cartridges 700 can be accessed. The floors 765 can be configured to hold any variety of different numbers of cartridges 700. For example, each floor can accommodate 1 to 4 (or more) plates 700.

Figure 8A:
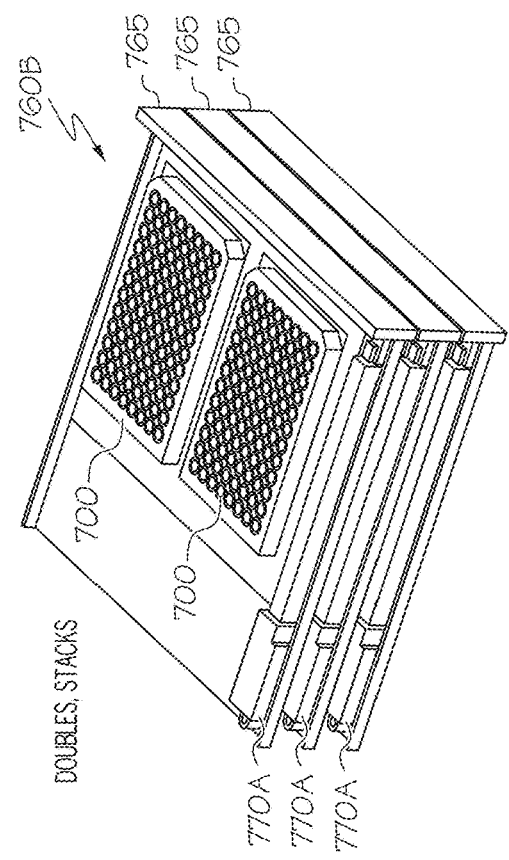
FIG. 8A is a perspective view of an incubation system with a tray holding two cartridges.
Figure 8B:
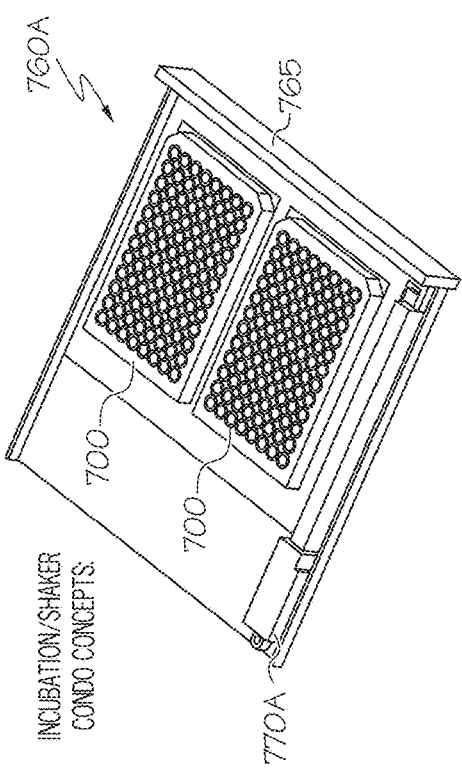
FIG. 8B is a perspective view of an incubation system with three stacked trays, each holding two cartridges.
Figure 8C:
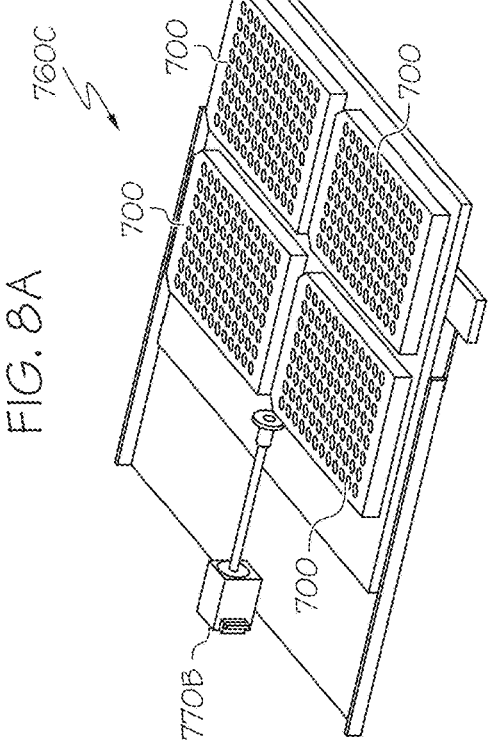
FIG. 8C is a perspective view of an incubation system with a tray holding four cartridges.
Figure 8D:
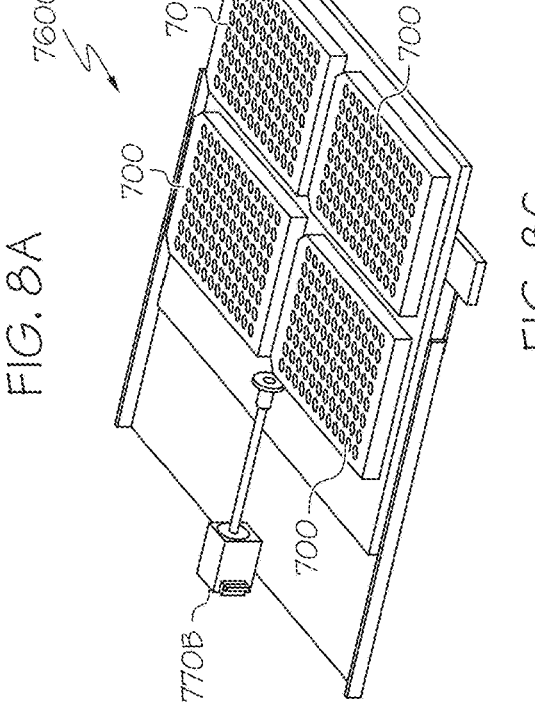
FIG. 8D is a perspective view of an incubation system with three stacked trays, each holding four cartridges.

As depicted, the incubators can include displacement mechanisms (e.g., actuators) to drive movement of the various floors so that the cartridges thereon can be accessed. For example, the actuators can selectively push one or more of the floors to open the hotel and slide out a floor so that the cartridges can be removed for processing by the system, such as sample separation or optical analysis. Referring to FIGS. 8A and 8B, the incubator can include a linear actuator 770A for the floors 765. Referring to FIGS. 8C and 8D, the incubator can include a rotationally based actuator 770B, such as a servo or stepper motor connected to a threaded rod engaged with a complementary threaded nut to open and close doors or covers of the incubator. As the actuator 770B rotates the threaded rod, the nut can travel axially along the rod, toward and away from the actuator. In some cases, the system can be configured such that the floors remain general fixed and the robotic gripper is configured to reach into the incubator and retrieve the cartridges While the systems have generally been described as implementing sample agitation (e.g., shaking) in association with the incubator, other examples are possible. For example, in some embodiments, the testing system can include one or more stand-alone agitation subassemblies. Unless otherwise stated, the stand-alone agitation subassemblies can include the agitation systems described herein associated with the incubator (e.g., the actuator 770A or actuator 770B).

In some embodiments, each floor has separate temperature control and temperature feedback. A temperature monitoring system (e.g., a thermocouple, thermistor, or semiconductor based temperature sensors) can be used for temperature feedback. In some cases, a proportional-integrative-derivative (PID) controller can be used to control temperature. Proportional (P), Integral (I), and Derivative (D) gains are typically optimized to achieve appropriate heating rate and reduce temperature fluctuations (e.g., oscillations around a target temperature) since certain antimicrobials are not stable at temperatures higher than 35 degree Celsius. In some embodiments, temperature control can be achieved convectively by circulating hot air. In some cases, both convection and conduction heating can be used. Additionally or alternatively, relative humidity can be controlled to reduce (e.g., minimize) liquid evaporation from cartridges. For example, the systems can be configured to limit evaporation from a well in a cartridge to equal to or less than about 2% of the initial liquid volume over a time period, such as 3 hours. In some embodiments, the system can control humidity in the incubator to about 80% within about +/−10%.

Sample Separation

In some embodiments, a separation (e.g., centrifugation) step is used to separate unbound amplifier from microorganism surface, for example, using the centrifugation subsystem 100 or magnetic separation subsystem 101 described above. Centrifugation utilizes differences in densities of microorganisms and surrounding fluid to create microorganism pellet. As one skilled in the art would appreciate, these separation methods use relative centrifugal forces (RCF) of 100 to 20,000 g's (where g is Earth's gravitational acceleration) can be used. The larger the RCF, the shorter the time for separation is typically needed. Typical ceiling value (e.g., the highest expected reasonable value) for cartridges, such as 96- or 384-microwell plates, is about 5,000 g's to reduce the likelihood of the cartridges physically degrading, for example, chipping or breaking. In some embodiments, the centrifugation subsystem can generate the desired relative centrifugal forces generated in the centrifugation systems that can be from about 2,000 g to about 5,000 g (e.g., about 2,500 g to about 4,000 g (e.g., about 2,500 g)). In some embodiments, the centrifugation can be performed for at least 2.5 minutes. In some cases, the 2.5 minutes can include the time to achieve the desired centrifugation speed (e.g., ramp-up time), which can be, for example, about 45 seconds. Configuring the separation system to be a centrifugation system design can allow samples (e.g., the cartridge) to be accessed more easily by a robotic gripper to load and unload cartridges. This helps to allow full automation of sample processing. In some embodiments, the centrifugation system can be configured to accommodate multiple plates per centrifuge rotor position (e.g., by stacking plates on each other). Such stacking permits simultaneous centrifugation of at least 4 cartridges and up to 16 cartridges in a 4-position centrifuge. In some cases, if an odd number of cartridges are being processed, one or more ballast plates can be used to balance the centrifuge. Commercially available centrifuges, which can be compatible with robotic loaders, that can be modified to be compatible and implemented with the testing systems described herein are made by Hettich Lab Technology of Beverly, Mass. and Tuttlingen, Germany, US; BioNex Solutions, Inc. of San Jose, Calif., US, and Agilent Technologies of Santa Clara, Calif., US.

Alternatively or additionally, as discussed herein, in some embodiments, pelleting of microorganisms can be accomplished using magnetic separation. For example, magnetic particles, which can be nanometer and/or micrometer size, with appropriate surface functionalization can be added to bind to microorganism surface. Binding of end point assay can be done simultaneously with magnetic particle binding (competitive assay) or after magnetic capture (either as binding to a pellet or after resuspension in solution). In some cases, magnetic capture can be retractable to allow resuspension and can be incorporated in a stand that allows orbital or axial agitation. Alternatively or additionally, in some cases, separation can be done using vacuum filtration. Alternatively or additionally, in some cases, separation may not be necessary to separate unbound probes.

Optical Systems

The testing systems herein include optical systems to interrogate growth of microorganisms in cartridges. For example, optical systems typically include an excitation light source, one or more filters, light collection optics, and one or more detectors. In some embodiments, optical signals can be measured using detectors in the form of a photomultiplier tube (PMT). The gain of the PMT is adjusted based on the optical signals detected from control wells within the cartridges to allow for a broad dynamic range.

The excitation light source can include any of various light emitting components. For example, in some embodiments, the excitation source can include a xenon lamp. Other examples of possible excitation light sources can include broadband light sources, such as tungsten halogen lamps, light emitting diodes (LEDs), and lasers.

Sets of filters or monochromators (e.g., diffraction gratings) for excitation and emission can be designed and configured according to the reagents used in the testing and the amplification chemistry being applied. For example, in some cases where resazurin is used, excitation filters can be used to excite the sample with light at a wavelength of about 560 nm and emission filters can be used to detect light emitted from the sample at about 590 nm (e.g., after reduction to resorufin). In another example, in cases where lanthanide based amplifiers are used, time-resolved fluorescence (TRF) or time-gated luminescence (TGL) can be used. In another example, in cases where Europium (e.g., europium cryptate) is used, excitation filters can be used to excite the sample with light at a wavelength of about 330 nm (e.g., with band of 80 nm) and emission filters can be used to detect light emitted from the sample at about 615 nm (e.g., bandwidth of 10 nm). Excitation and detector are typically synchronized since TGL uses short pulses and delayed time windows for measurement due to long lifetime of lanthanide reporter molecules. For example, for Europium, a delay of 100-200 microseconds (µs) can be used between extinction of the excitation light source and the start of measuring the light emitted by the sample. For example, a 200-600 µs period of measuring the light emitted by the sample (i.e., integration window) can be used.

Readout electronics for the optical detectors (e.g., PMT) can allow for both analog and digital outputs. In both modes, current output of PMT is converted using a transimpedence amplifier that can allow variable amplification. In digital mode, output of the amplifier can be fed into a comparator (e.g., discriminator) with a variable threshold and pulse-shaper that convert an input signal into a signal of digital pulses (e.g., square wave) which can then be counted. This digital signal can conform to various digital voltage level conventions (e.g., TTL, CMOS). The number of digital pulses generated thus corresponds to the number of photons getting to the detector. A separate photodiode can be used to normalize the photon count to incident light energy and minimize variations between excitation pulses (e.g., by splitting incident light using a dichroic mirror). Alternatively or additionally, in some embodiments, the optical detector is a CCD sensor, a CMOS sensor, an Avalanche Photodiode, or a silicon photomultiplier or arrays thereof for simultaneous readout of plurality of wells. In some embodiments, current output from a PMT can be fed into a gated charge integrator followed by a digitizer. Integrated signal during integration window corresponds to the incident light energy emitted from the sample. Alternatively, or additionally, peak detection of output signal from the charge integrator can be used as a proxy for emitted light energy from the sample.

In some cases, the optical detectors can measure fluorescence at excitation and emission wavelengths and bandwidths compatible with one or more commercially available reagents, such as resazurin and/or Thermo Fisher Alamar-Blue® Cell Viability Reagent, when dissolved in suitable solvents and then metabolically reduced to form Resorufin (i.e., a metabolic assay). As discussed below, the systems herein can include an excitation filter of 560 nm with 15 nm bandwidth and emission filter of 590 nm with 20 nm bandwidth. In some embodiments, have a fluorescence detector sensitivity range from 10 pM to 100 µM Resorufin. In some embodiments, the optical detectors can have a sensitivity range from 40 fM to 600 nM Europium, for example, for binding assays.

In some embodiments, the optical detectors can feature a software-adjustable gain of the TGL detector. This allows the optical detectors to automatically adjust the gain for each cartridge based off the low and high calibrator wells to optimize the measured signal. In some cases, the optical detectors dynamically set the TGL detector gain and scaling based on the signal measured in each a high and low calibrator well such that the low calibrator signal is at about 5-10% of the detector range and the high calibrator signal is at about 90-95% of the detector range. These two wells represent the minimum and maximum extents of the measured signal. 5% and 95% can be used to permit measurement of wells which can fall slightly outside the signal range of the calibrators. The optical detectors can have a fluorescence detector sensitivity range from about 40 fM to about 600 nM Europium. Currently, the minimum suitable sensitivity for the assay chemistry is 365 nM Europium. However, sensitivity below 365 nM Europium is desirable to support continued assay optimization and future reductions in AST processing time.

The detector can be configured to measure TGL with a 100 µs+/−10 µs excitation flash duration. In some cases, the detector can measure TGL using a 200 µs+/−20 µs delay after excitation before measuring the emission. In some cases, the detector can measure TGL using a 300 µs+/−30 µs time for integration of the emission signal on the detector. In some cases, the detector can measure TGL at excitation and emission wavelengths compatible with Cisbio Europium cryptate NH2 when dissolved in water. For example, the Cisbio Europium cryptate NH2 reagent can be available as Cisbio part #65EU2ABB. In some examples, the optical systems can use an excitation filter of 330 nm with 80 nm bandwidth and emission filter of 615 nm with 8 nm bandwidth. In some cases, the detector can measure the TGL of all wells in a 96-well cartridge in less than about 1.5 minutes. This time can include the time to measure the calibrator wells and perform gain adjustment. In some cases, the detector can measure the TGL of all wells in a 384-well cartridge in less than about 6.0 minutes. This time can include the time to measure the calibrator wells and perform gain adjustment. In some cases, the detector can perform TGL excitation and emission from the top of the cartridge. As discussed above, this can permit the use of opaque cartridges.

In some embodiments, optical systems described herein can be configured to measure the fluorescence of all wells in a 96-well cartridge in less than about 1.0 minute. In some cases, the optical systems can be configured to measure the fluorescence of all wells in a 384-well cartridge in less than about 4.0 minutes. As depicted in the examples illustrated and described herein, the optical system is typically configured to perform fluorescence excitation and emission from the top of the cartridge (e.g., above the wells). This helps to permit the use of opaque cartridges. In some embodiments, systems can be configured to excite and measure light from multiple wells simultaneously (e.g., 2, 3, 4, 5, 6, 7, 8, 9, 10, 11, 12, 13, 14, 15, 16, 17, 18, 19, 20, 21, 22, 23, or 24 wells). In some embodiments, systems can be configured to excite and measure light from two or more sets of rows of multiple wells simultaneously. For example, an optical system can include an optical head having two rows of components to be positioned over the wells. In some embodiments, excitation and measurement of adjacent well can be delayed to reduce (e.g., minimize) crosstalk. In some embodiments, wells can be made of opaque material to reduce or eliminate crosstalk of adjacent wells. In such cases, excitation and measurement of emission of adjacent wells can be done simultaneously.

Optical systems can include various configurations of light delivery and transmission. In some embodiments, referring to FIG. 9A, an optical system 900 includes an excitation source is coupled to a fiber bundle assembly (e.g., a bifurcated fiber bundle) 910 having an emission portion 910A and an excitation portion 910B. The bifurcated fiber bundle can have two fiber bundles disposed in a common end and separate into two legs (e.g., the emission portion 910A and the excitation portion 910B) at the other end. The fiber types used in each leg can be the same or different, allowing optimization of fiber core diameter or wavelength range based on the application. The two-path fiber assembly 910 with two separate light paths allows for use of different optical filters depending on desired excitation and emission wavelengths of reporter molecule. Light from an excitation source 920 is directed into a well 710 of cartridge and focused using appropriate optical elements (e.g., lenses) 970. The same optical system can be used to collect light from the well 710 and guide it to a detector 930. In some embodiments, an optical system includes an optical head having multiple fiber bundles to interrogate multiple wells of a cartridge. For example, an optical head can include an array of fiber bundles whose distal ends are spaced apart from one another and configured to align with wells of the cartridge. For example, the optical head can have one or more rows of fiber bundle distal ends (e.g., two rows of 8 fiber bundles) to be positioned over the wells. Appropriate emission filters 940 can be used to select or filter wavelengths of light received and measured by the detector 930.

Additionally, appropriate excitation filters 941 can be used to select or filter wavelengths of light directed to the sample.

Figure 9B:
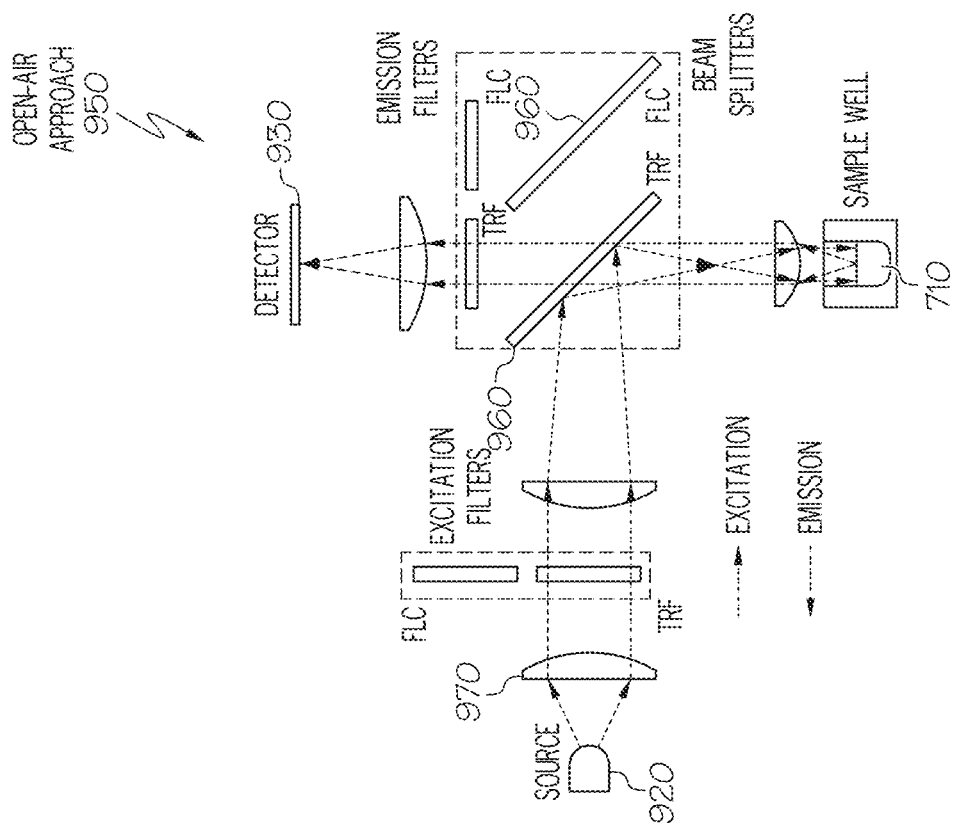
FIG. 9B is a schematic view of an example optical system, formed of multiple lenses and mirrors to deliver and detect light.
Figure 9A:
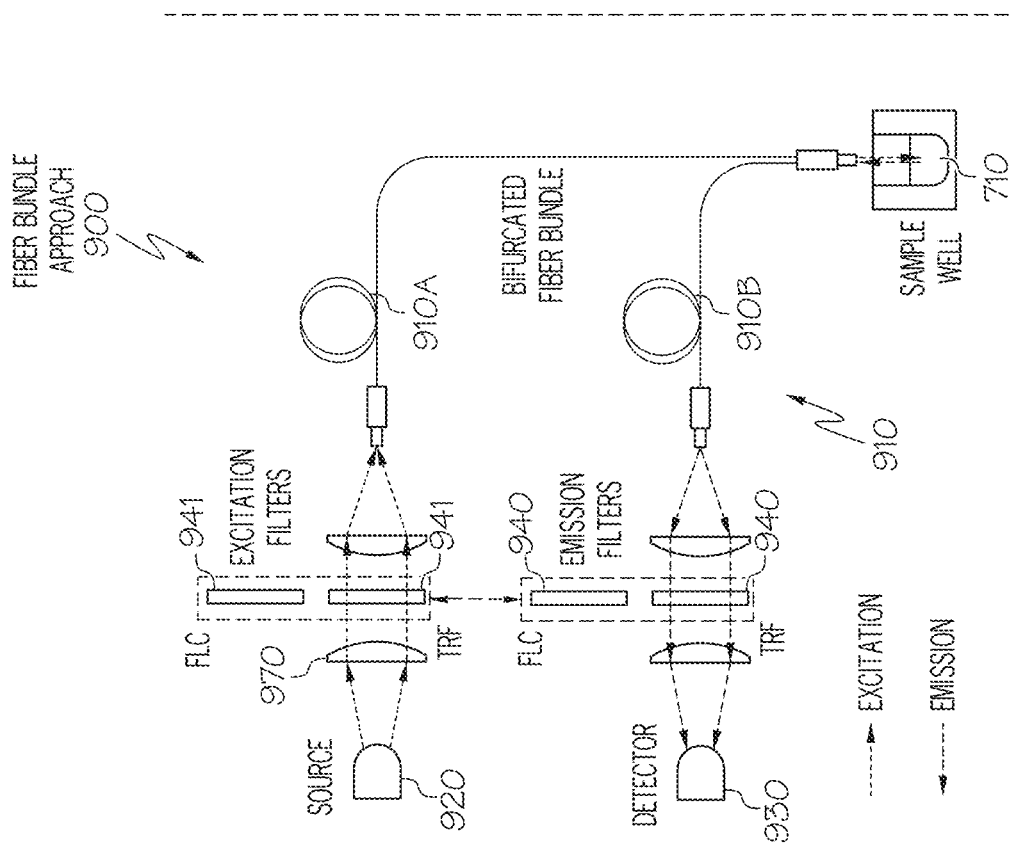
FIG. 9A is a schematic view of an example optical system, formed of a fiber bundle and mirrors to deliver and detect light.
Figure 16B:
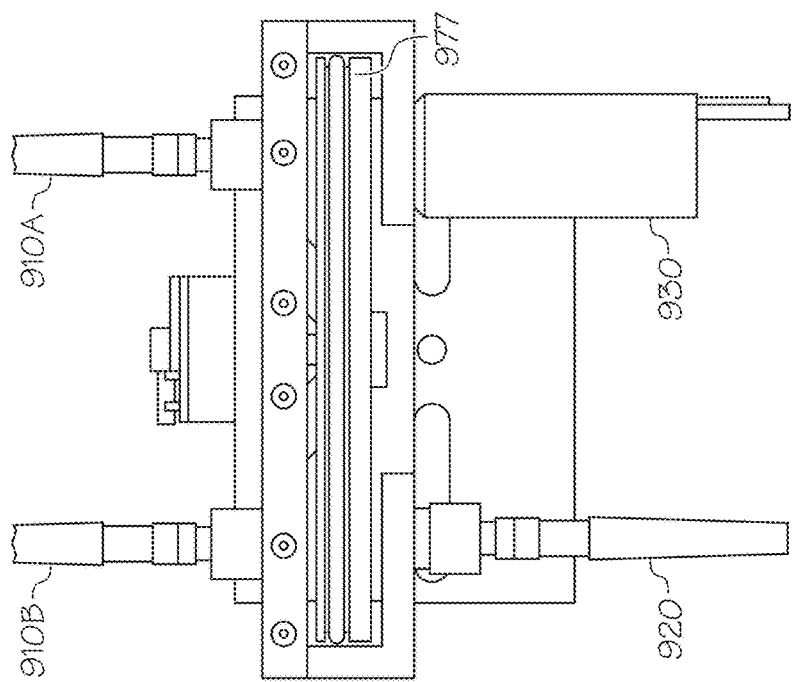
FIGS. 16A and 16B are perspective and top views, respectively, of an optical system having component to index optical filters used to excite light provided to, and to interrogate light emitted from, a sample.
Figure 16A:
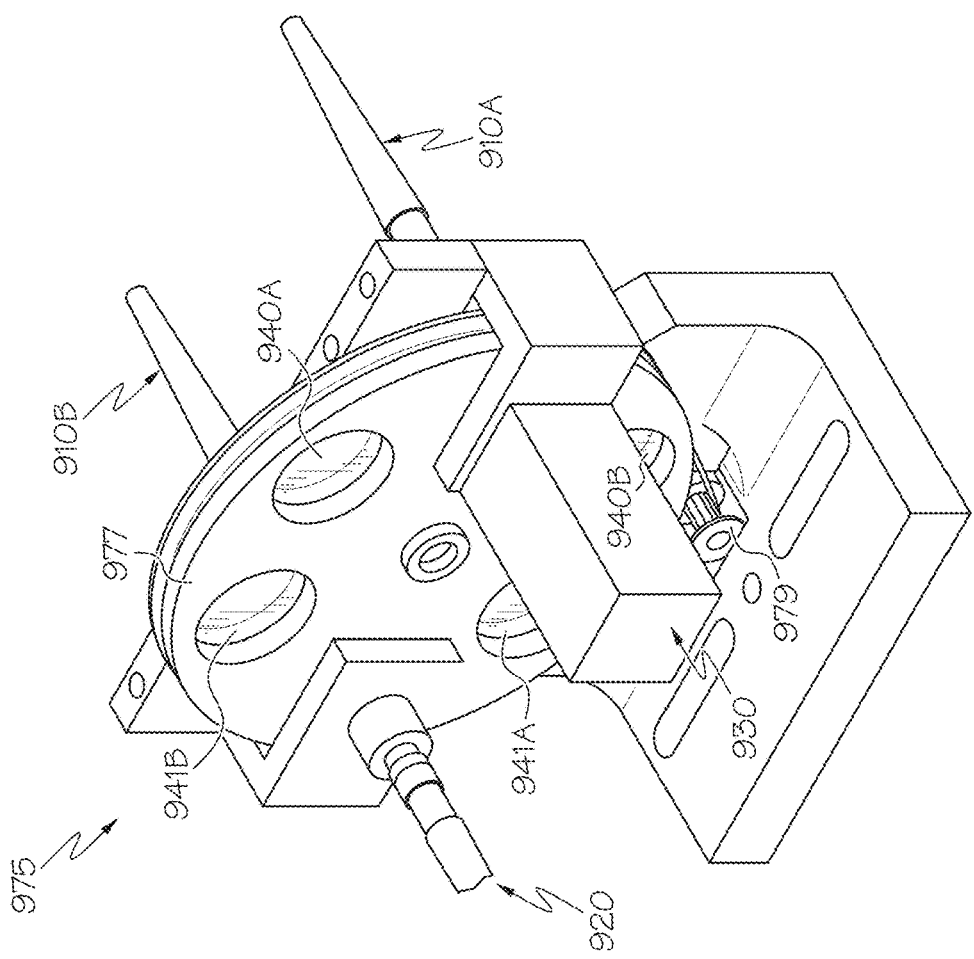

Briefly referring to FIGS. 16A and 16B, an optical system 975 can include an excitation source that is coupled to a fiber bundle assembly (e.g., a bifurcated fiber bundle) 910 having an emission portion 910A and an excitation portion 910B, which can be similar to the system 900 described and illustrated in FIG. 9A. However, in some embodiments, optical systems include a system to adjust or change the optical filters in order to perform one or more assays utilizing different light wavelengths for either excitation of a sample or emission of light from a sample. For example, a system can include an indexing component (e.g., an indexing wheel) 977 configured to change both the excitation and emission filters (e.g., at the same time). In some embodiments, the wheel 977 can be indexed in between two different assays being performed to provide the desired optical filters. In some cases, the system can include a set of two optical filters (e.g., a first excitation filter 941A and a first emission filter 940A) disposed on the indexing wheel 977 which is configured to selectively position a first optical filter (e.g., the first excitation filter 941A) in line with the excitation source 920 and a second optical filter (e.g., the first emission filter 940A) in line with the optical detector 930. The indexing wheel 977 can include other sets of two filters (e.g., a second excitation filter 941B and a second emission filter 940B), where an indexing motion of the indexing wheel 977 replaces the optical filter in-line with the excitation source and the optical filter in-line with the optical detector. In some cases, the individual filters of a set can be positioned at opposite sides of the wheel 977. In some embodiments, the wheel 977 can be a six position indexing wheel for positioning up to six combinations of sets of optical filters. The indexing component can be configured to index at any of various speeds and by any of various techniques. For example, the system 975 can include a motor 979 coupled to the wheel 977, for example by a belt, to rotate the wheel 977 and change the filters.

Other embodiments are possible. For example, referring to FIG. 9B optical detection systems 950 can be configured so that excitation, detection, and data processing are performed within the same subassembly in which the cartridge can be loaded using the robotic gripper. The optical detection system 950 can include an optical excitation source 920 configured to produce and emit an optical signal to the sample in a well 710 and a detector 930 to receive an optical signal from the sample. The system 950 can include a system of reflectors (e.g., mirrors) 960 and lenses 970 to direct light to the sample well 710.

In some embodiments, the optical subsystem includes an x-y stage (e.g., a robotic gantry or translating table) that allows detector to interrogate each well of the test panel. For example, the x-y stage can move a cartridge relative to the detector so that the detector can be positioned above all of the different wells of the cartridge for processing each of the samples. Alternatively or additionally, the cartridge can be configured to remain in place (e.g., static) while detector moves relative to the cartridge.

Each cartridge can contain a combination of antimicrobials and a defined twofold dilution series of each antimicrobial. In addition, each cartridge can contain control wells, such as a growth control well, a no growth (contamination) control well and a saline control well. The saline control well can represent FIT control approximately equal to the initial concentration of microorganism in inoculum. The cartridges can include multiple wells (e.g., 96 well cartridge or 384 well cartridge) with a cover (e.g., a removable lid) and an identifier (e.g., a bar code) that uniquely defines antimicrobial configuration and a unique code, which defines the plate and can be associated with a unique sample conforming to HIPAA. Once a MIC and CLSI breakpoint is found, the system can allow visualization of this result using a graphical user interface and communication with LIMS.

In some embodiments, the testing system 50 includes a separate waste tray where the processed cartridges can be discarded. For example, once the end point assay is completed, the test panels can be analyzed (e.g., measured). Processed cartridges can be discarded after analysis. In some embodiments, the cartridges can be discarded automatically, for example, using the robotic transfer system 200. In some embodiments, the processed cartridges can be discarded by being loaded back on the loading station 300 where a user can remove them from the system and discard them appropriately.

Example System

Figure 10:
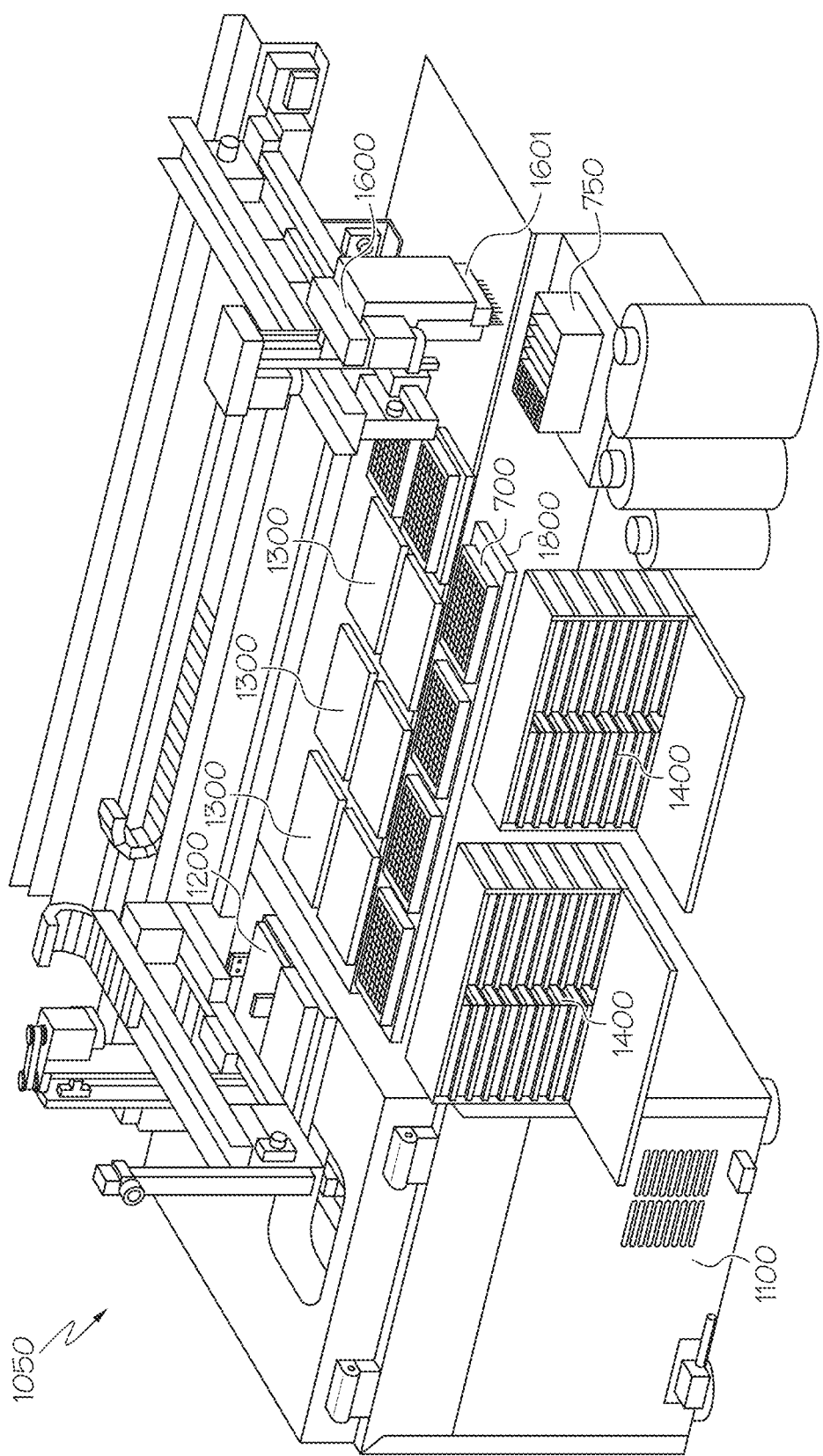
FIG. 10 is a perspective view of an example antimicrobial susceptibility testing system.

FIG. 10 is a perspective view of an example antimicrobial susceptibility testing system 1050. The testing system 1050 can include a robotic gripper (e.g., of the robotic transfer system 1200) to handle sample cartridges 700 within the system, one or more incubation subassemblies 1400, a liquid handling subassembly 1601 controlled by a robotic system 1600, a centrifugation subassembly 1100, as well as any of the various subassemblies and components discussed above with respect to the other example testing systems. In some embodiments, the system 1050 includes a platform (e.g., staging area, (e.g., stage)) 1800 to act a cartridge placement or holding area. For example, stage 1800 can be disposed between an incubation subassembly 1400 and an agitation system 1300. In some cases, the stage 1800 can be configured to raise and lower with respect to other components, such as the incubation subassembly 1400. For example, the stage can be mounted on one or more actuators. Unless otherwise stated, the components and subassemblies of the testing system 1050 can be the same or similar to the components discussed with respect to the other example testing systems.

Figure 11:
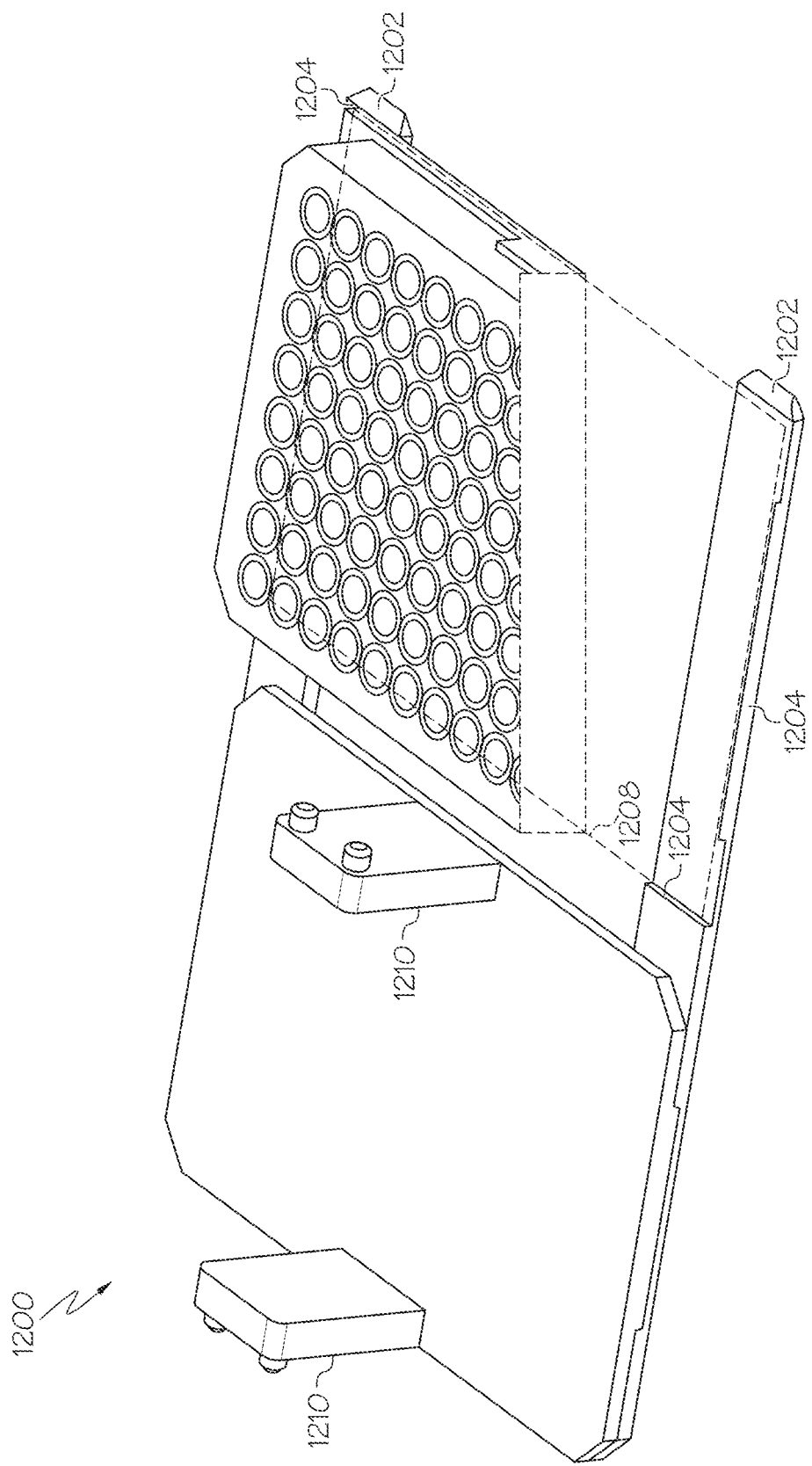
FIG. 11 is a perspective view of an example cartridge handling component, illustrating a cutaway view of a cartridge thereon.

FIG. 11 is a perspective view of an example cartridge handling component 1200. As discussed above, robotic transfer system (e.g., a 3-axis robotic arms) 1200 can include one or more cartridge gripping or carrying components. For example, in some embodiments, the cartridge robotic transfer system 1200 includes a set of lifting fingers 1202 sized and configured to support a cartridge 700 (which is shown cutaway). The set of fingers 1202 can define one or more lateral cartridge positioning features (e.g., vertical ridges) 1204 to limit a cartridge from inadvertently sliding off of the transfer system 1200 during movement of the cartridge. The fingers can be positioned substantially parallel to one another and be separated to accommodate one or more surfaces on which the cartridge is to be placed. In some cases, the fingers can be separated by at least about 2 inches (e.g., at least about 3 inches). In some cases, the positioning features 1204 can be positioned to define an opening (e.g., a platform recess) 1208 that has a footprint that corresponds to that of the cartridge. For example, each finger 1202 can have a positioning feature 1204 along its outermost side edge.

In effect, the transfer system 1200 and the lifting fingers 1202 can serve as a forklift to grip and handle the cartridges within the system. In some embodiments, the lifting fingers 1202 include a beveled or angled from tip to aid in sliding under a cartridge. In some embodiments, the lifting fingers 1202 are resiliently formed such that they can deflect under a cartridge return to their initial position once the cartridge is fully positioned in the opening 1208. The lifting fingers 1202 can also be configured to be thin (e.g., have a low profile) in order to reach into tight spaces, such as within the incubation subassembly, to retrieve the cartridges. The transfer system 1200 can also define one or more mounting features (e.g., interfaces) 1210 by which the robotic arm can couple to the transfer system 1200. For example, the retention elements 215 of the gripper arms 203 can couple to the interfaces 1210 when the arms 203 are articulated to close and grip the system 1200. In some embodiments, the fork lift-style transfer system 1200 and the lifting fingers 1202 can be used in combination with the gripping mechanism 201 when cartridges are being inserted into and removed from area with low clearance height, such as the incubation subsystem 1400 discussed below. In some embodiments, the gripping mechanism 201 itself (e.g., the arms 203) are used to grip a cartridge directly when the cartridge is to be delivered to or retrieved from deep areas, such as within the centrifuge.

Figure 12:
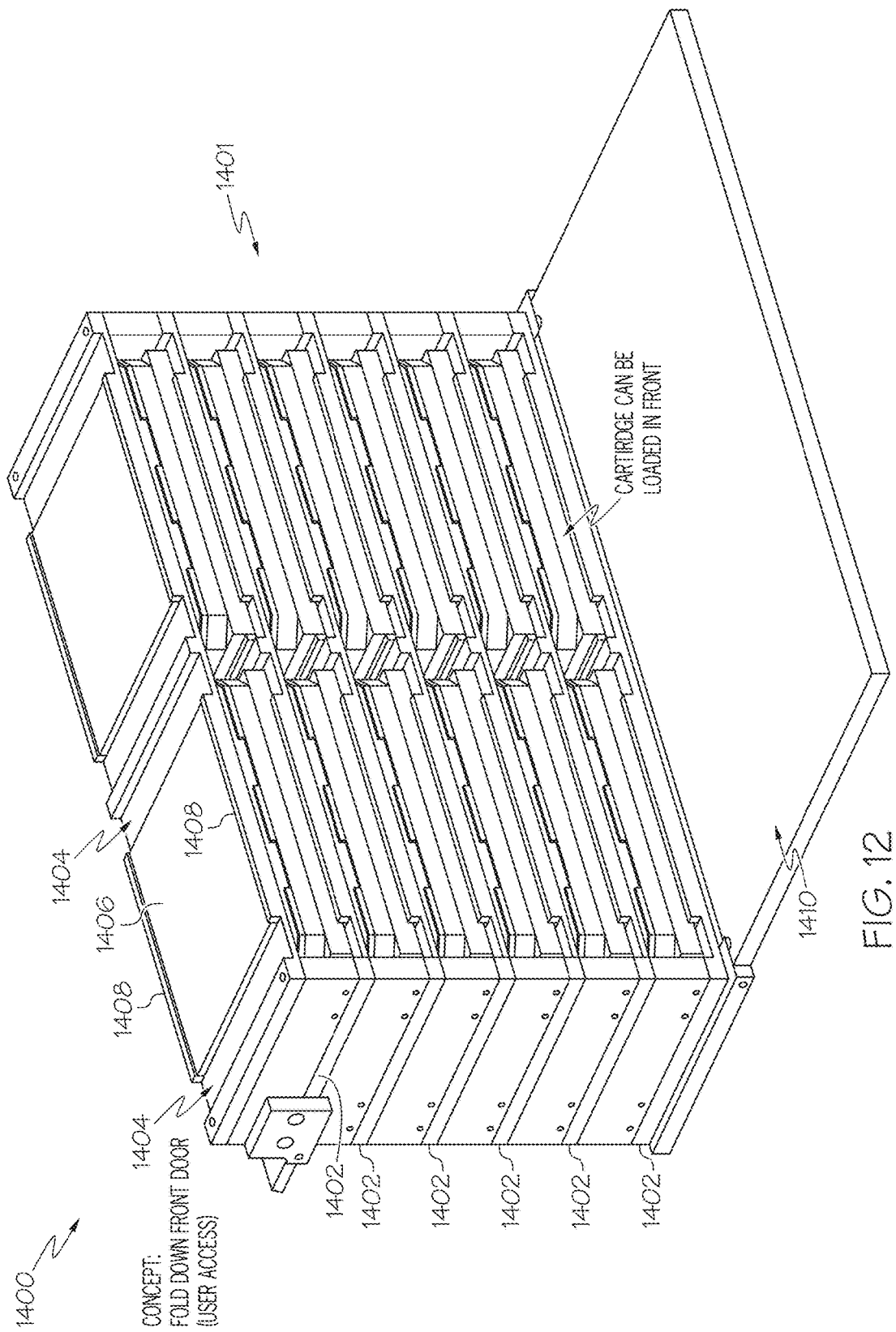
FIG. 12 is a perspective view of an example incubation subsystem for use in an antimicrobial susceptibility testing system.

FIG. 12 is a perspective view of an example incubation subsystem 1400 for use in the antimicrobial susceptibility testing system 1050. In some cases, the testing system 1050 can include more than one (e.g., two) incubation subsystems 1400. As depicted, the incubation subsystem 1400 can be configured to house multiple cartridges (e.g., 12 cartridges). For example, the incubation subsystem 1400 can include a tiered structure having a tower 1401 with multiple floors 1402, where each floor 1402 can accommodate one or more cartridges for incubation. The floors 1402 can be configured to interface with the robotic cartridge carrier (e.g., the lifting fingers) 1202. For example, for each cartridge to be housed, the floor 1402 can define one or more (e.g., a pair) of recesses 1404 sized and configured to accommodate the lifting fingers during deposit or removal of a cartridge from the incubator. For example, the recesses 1404 can have a width and height that is larger than those of the fingers. In some cases, the recesses 1404 can have a height that is sufficiently large enough such that when the fingers place the cartridge on a stage 1406 of the floor 1402, the fingers 1202 can be lowered into the recesses 1404 with adequate clearance so that they can be removed (e.g., slid out) without disturbing the cartridge. In some embodiments, the floor 1402 defines a positioning element (e.g., vertical ridge) 1408 along its front or back end, such as along the stage 1406 to limit the cartridge's ability to inadvertently slide or fall out of the floor 1402. Thus, the fingers 1202 can insert the cartridge into the incubator above the ridge 1408, lower the cartridge onto the stage 1406 once the cartridge has cleared the ridge 1408, lower the fingers 1202 until they are deep enough into the recess 1404 so that the cartridge is far enough away from the fingers 1202 so as to clear the positioning features 1204, and then the fingers 1202 can be removed from the incubator.

The incubator 1400 can include a cover (e.g., a door) 1410 that can be opened and closed to contain the cartridges during incubation. In some cases, the door 1410 and/or a frame of the incubator can include one or more rotational stops to limit the door 1410 from traveling or opening beyond a desired stop point. In some cases, the stops can cause the door 1410 to serve as a shelf in front of the cartridges. In some examples, the user can open the door 1410, manually place cartridges to be tested in the incubation subsystem 1400, and close the door. Additionally, the incubation subsystem can include any of various heating systems and/or agitation subsystems. For example, in some embodiments, the floors 1402 can include a heating element in or along the stage 1406 along which the cartridge is disposed during incubation. In some case, by stacking floors 1402 on top of one another, cartridges can be sandwiched in between two floors and thus be heated from the top and bottom.

Cartridges can be inserted and removed from the incubator 1400 in any of various ways. For example, in some examples, a user can load cartridges through the front (e.g., by opening the door 1410) and the testing system can remove cartridges from the incubator 1400 from an opposite side (e.g., the back side). Additionally or alternatively, the testing system can remove cartridges from the front of the incubator.

Figure 13:
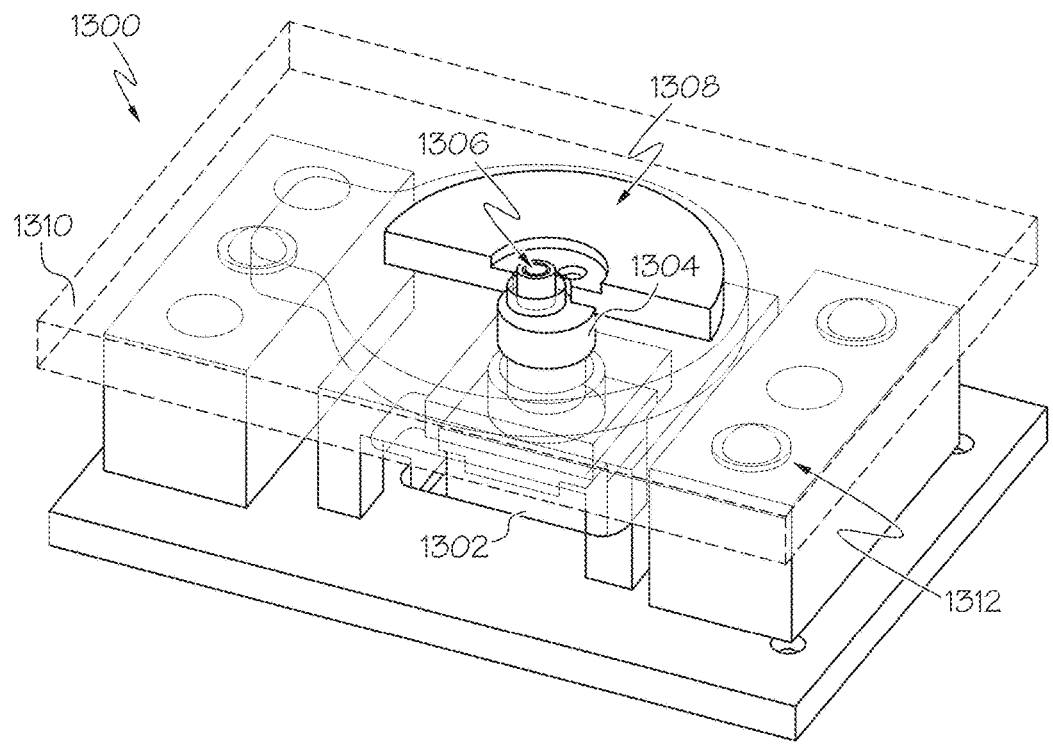
FIG. 13 is a perspective view of an example sample shaking subsystem having a rotating oscillating component.

FIG. 13 is a perspective view of an example sample shaking subsystem (e.g., rotational agitation system) 1300 having a rotating oscillating component. The shaking subsystems can be used in association with the incubation subsystems or as stand-along subassemblies. In the example of FIG. 10, agitation subsystems can be used for both one or more incubation subsystems 1400 and as one or more stand-alone systems 1300. The rotational agitation sub system 1300 can include a motor (e.g., servo) 1302 that spins a rotor 1304 having an off-center (e.g., eccentric) interface 1306, such as a cam device, that imparts a rotational, oscillating motion onto a cartridge when the motor 1302 spins in accordance with the various agitation methods described above. In some cases, the rotor 1304 can include a counter balance weight to reduce or limit vibrations during agitation. The rotor 1304 can interface with a platform 1310 that moves along the oscillating path with the interface 1306. In some examples, the platform 1310 can be disposed along one or more bearing surfaces to provide smooth and undisrupted translation along its oscillating path. For example, in some cases, the platform 1310 can be disposed on one or more bearings (e.g., rollers) 1312.

Figure 14:
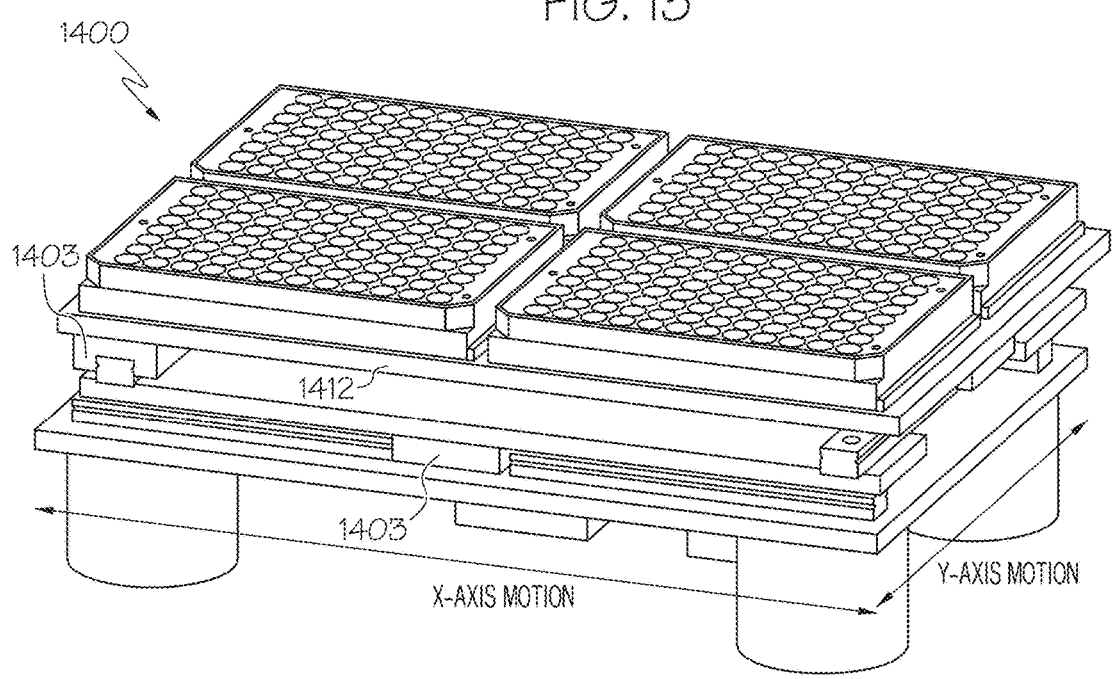
FIG. 14 is a perspective view of an example sample shaking subsystem having a set of multidirectional linear actuators.

Additionally or alternatively, the testing system 1050 can include shaking subsystems that utilize linear motion to generate sample shaking. For example, referring to FIG. 14, a sample shaking subsystem (e.g., multi-directional agitator) 1400 can include one or more (e.g., a set of two) multidirectional linear actuators 1403 that can drive a platform 1412 in multiple directions. The set of actuators 1403 can be positioned in various configurations. For example, the actuators 1403 be positioned substantially perpendicular with respect to one another. In cases where a circular or orbital agitation is desired, the two actuators can move in sequence with one another to cause the cartridges to travel along the desired radius and speed.

Figure 15:
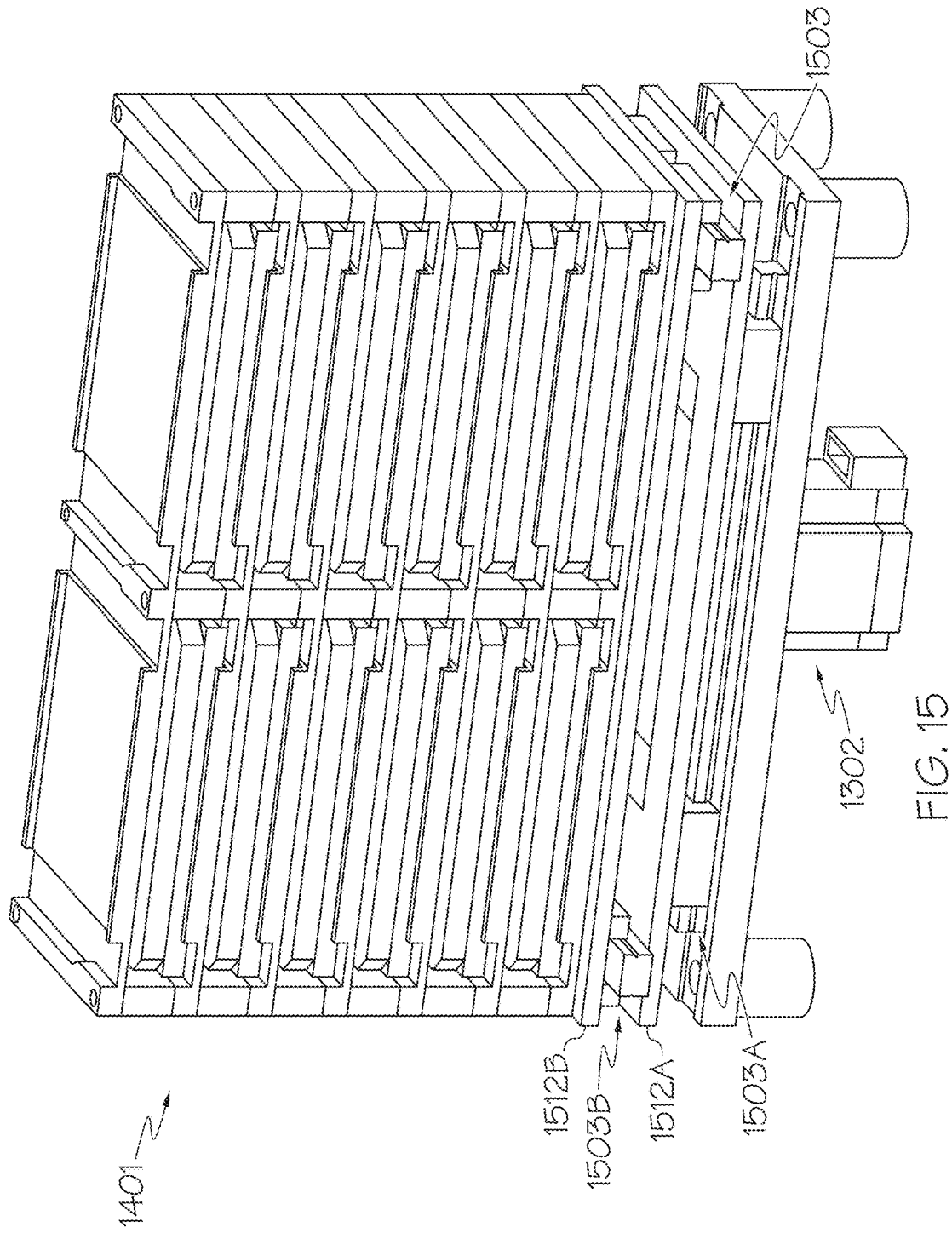
FIG. 15 is a perspective view of an example sample shaking subsystem having a rotating oscillating component and a set of multidirectional linear bearing surfaces.

Additionally or alternatively, the testing system 1050 can include shaking subsystems that utilize a combination of rotational and linear motion to generate sample shaking. For example, referring to FIG. 15, a sample shaking subsystem (e.g., multi-directional agitator) 1500 can include two or more (e.g., two sets of two) multidirectional linear friction reducing components (e.g., linear bearing surfaces) 1502 along which different platforms 1512 can slide in combination in order to permit the tower 1401 and cartridges therein to travel along an orbital path that can drive a platform 1512 in multiple directions. In some cases, the bearing surfaces can include linear bearing rails and sliding stages configured to slide along the bearing rails. For example, a first platform 1512A can be configured to slide relative to a base along a first set of bearing surfaces 1503A, such as along an x-axis. A second platform 1512B can be configured to slide relative to the first platform 1512A along a second set of bearing surfaces 1503B, such as along a substantially perpendicular y-axis. The combined linear motion along different axes and be used to generate a substantially orbital motion. To drive the tower 1401, the shaking subsystem 1500 can include a motor (e.g., servo) 1302 that spins a rotor having an off-center (e.g., eccentric) interface, such as a cam device, that imparts a rotational, oscillating motion onto a cartridge when the motor 1302 spins in accordance with the various agitation methods described above. In some cases, the rotor 1304 can include a counter balance weight to reduce or limit vibrations during agitation. While the rotational motion can be imparted by the motor 1302, the linear bearing surfaces can be used to constrain or guide the motion of the tower 1401.

Figure 19:
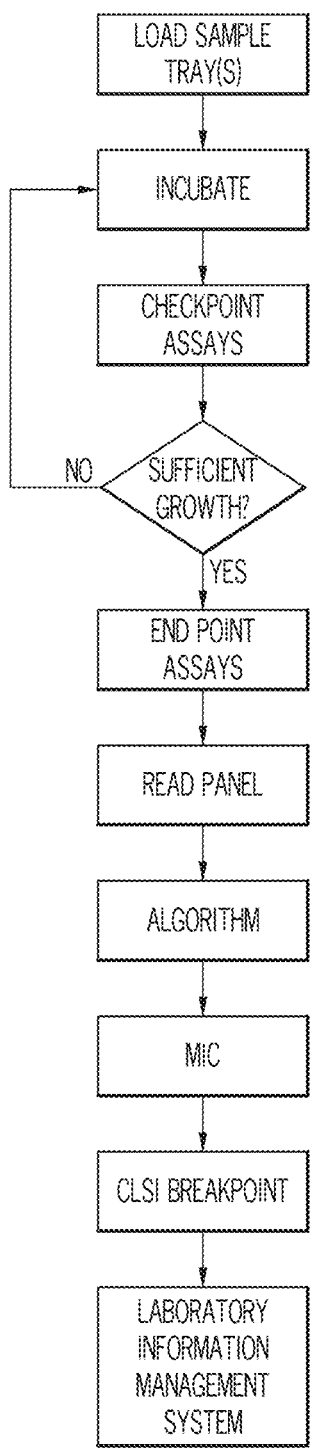
FIG. 19 is a flow chart of an example method of performing an example antimicrobial susceptibility testing sequence.

The example systems and components described herein can be used to carry out any of various antimicrobial susceptibility testing processes. As discussed above, the systems described herein can facilitate testing processes by which samples can be loaded in and the system can automatically handle the samples and required fluids for testing. An example method sequence is depicted in FIG. 19 and described below.

Prior to loading into the system, each sample (e.g., containing microorganisms (e.g., microorganism) for which susceptibility testing is to be performed) can be diluted and adjusted to a desired appropriate starting concentration according to CLSI standard (e.g., 3-7e5 CFU/ml (CFU=colony forming unit)). In some embodiments, the diluent is a growth media, such as Mueller-Hinton Broth. The sample and diluent can be added to the cartridge. As discussed above, in some cases, the sample and diluent can be added to testing wells (e.g., wells 1710*t*) and some of the control wells (e.g., growth well 1710*g*). In some cases, the diluent by itself (i.e., without added sample) can be added to one of the control wells (e.g., a no-growth well). Once the cartridge is inoculated and the cartridge identifier is read and associated with a sample, the cartridge (e.g., cartridge 700, 701) can be placed on a loading drawer (e.g., drawer 300) and loaded into the system. As discussed above, the loading drawer 300 can accommodate a plurality of test panels. Alternatively, the cartridge can be loaded directly into the incubation system (e.g., the incubation system 1400). As discussed above, a preheat can be performed before the cartridge is loaded into the incubation system.

In cases where metabolic dye is used for check point assay, the dye can be stored in cartridge during cartridge packaging process and can be added before or after inoculation of the said cartridge with sample or can be added by the system after loading. Once loaded into the system, in some examples, a robotic gripper (e.g., of the robotic transfer system 200) can move the cartridge to an incubator (e.g., the incubator 400). In other examples, the cartridges are loaded directly into the incubator (e.g., incubator 1400). A temperature of incubator can be adjusted between about 33° C. and about 39° C. (e.g., typically between about 33° C. and about 35° C.). If particular temperature-sensitive antimicrobials are not present on a cartridge, incubation temperature can be increased to promote faster growth. As discussed above, temperature sensors (e.g., thermocouples, thermistors or silicon based) can be used to provide feedback to temperature controller which in turn controls heater. Each incubator nest (e.g., nest 414) can allow heating from bottom and sides. In some cases, each incubator nest can allow uniform heating from the sides and bottom. For example, air circulation can be provided to allow for more uniform heating. Additionally, humidity can be controlled to reduce or limit evaporation of fluid. During incubation, shaking of the sample can occur, and orbital shaking speed can be adjusted using, for example, using driver system 420 having a motor, belts, gears, cams, etc., connected either directly or indirectly.

During incubation, the control wells (e.g., the growth control, the no growth control, and the FIT control) can be interrogated periodically (e.g., after a predetermined time) until the algorithm determines that sufficient growth is detected. Alternatively, system can be programmed to interrogate these wells only once after a certain time period (e.g., 3 hours) after the onset of incubation. For example, the system can interrogate (e.g., optically inspect) growth in the control wells (e.g., the growth well 1710g versus the no-growth well 1710ng). In some embodiments, this can include removing the cartridge from the incubator with a robotic gripper and using the optical system to observe growth within the growth well. In some embodiments, a cartridge can be removed from the incubator 1400 using the transfer system 1200 and the lifting fingers 1202 and the robotic arm-mounted optical system (e.g., system 900) can interrogate the control wells as soon as the cartridge is removed.

After this interrogation, the system determines whether to continue incubation to promote additional growth of the microorganisms before starting the end point assay or to start the end point assay. For example, by comparing signals from the growth well and the no growth well, as well as time evolution of growth, the system can determine when to initiate end point assay.

Figure 1C:
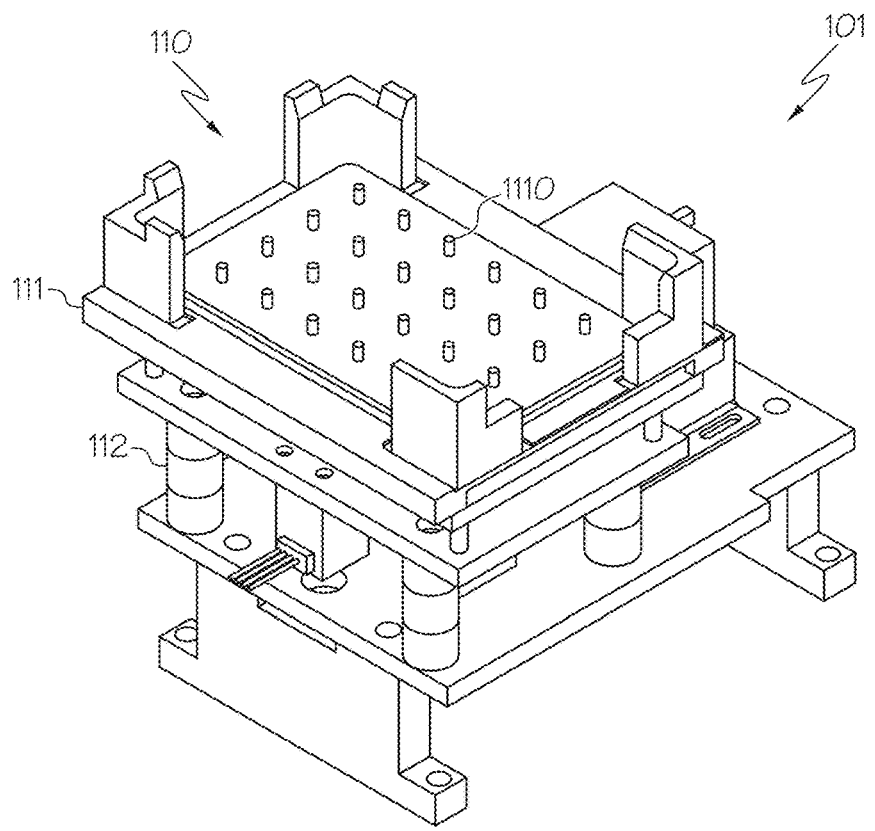
FIG. 1C is a perspective view of an example magnetic capture system.

Once the system determines that there has been sufficient growth of the microorganisms within the control wells and the end point assay can proceed, separation (e.g., centrifugation) can be performed to pellet microorganisms. For example, the system can place a cartridge into centrifuge 100 in the example of FIG. 1A, the centrifuge 1100 in the example of FIG. 10, or the magnetic capture separation system 101 in the example of FIGS. 1B and 1C. In some cases, the transfer system and lifting fingers 1202 can deliver the cartridge through an opening in the centrifuge 1100, for example, after interrogating the control wells without placing the cartridge back into the incubator 1400.

After the microorganism has been separated from the diluent, for example, using the centrifuge, the sample can undergo aspiration. Aspiration is useful to remove the diluent, which can improve background signal of the end point assay. For example, the robotic arm can retrieve the cartridge from the separation system so that the fluid handling system can remove some or all of the diluent. In some cases, the transfer system and lifting fingers 1202 retrieve the cartridge through an opening of the centrifuge 1100, and position the cartridge in a location accessible by the liquid handling subassembly 1601. In some examples, during liquid delivery or removal (and/or during optical analysis), the gripper can place the cartridge at any of various locations within the system. For example, the cartridge can be placed at an existing subassembly or a subassembly that is a specifically dedicated location that allows accurate liquid addition and aspiration (e.g., flatness, stability). In some cases, the cartridges can be placed on the incubator 1400, on the stand-alone agitation system 1300, or on the raising/lowering stage 1800. The liquid handling subassembly 1601 can then move to a location above the cartridge and lower such that the aspiration nozzles 604 enter wells so that excess fluid can be removed. As described with respect to FIG. 5C, the aspiration nozzles 604 can be position at different locations based on an expected location of the pellet.

Next, one or more solutions can be added to bind reporter molecule to microorganism surfaces. In some cases, the solutions can be added simultaneously or sequentially. The solutions can include any of various buffers, linkers, and/or reporter molecules (e.g., catalysts, amplifiers, etc.). In some embodiments, additional separation, aspiration, and wash steps can be performed to remove unbound reagents, reduce nonspecific binding, and increase signal-to-noise ratio. Depending on the reporter molecule being used, testing methods can also include addition of substrate reagent that generates an amplified signal. Agitation, such as shaking (e.g., orbital or axial) can be applied to speed up binding reactions. For example, after the fluid handling subassembly 1601 delivers the reporter molecules, for example using the reagent delivery nozzles 602, the transfer system and lifting fingers 1202 can place the cartridge back into the incubator 1400 or on the stand-alone agitation system 1300.

In some embodiments, the cartridge and samples are returned to one or more assemblies for further agitation or incubation. For example, the cartridge can be placed back into the incubator 1400 or on an agitation system 1300. In some embodiments, the cartridge and samples containing the metabolic probe can be placed back into the incubator for about 1 hour.

The optical signal can then be measured. The optical signal can be generated from any of various sources, such as absorbance, fluorescence, time-resolved fluorescence, chemiluminescence, electrochemiluminescence, or photon upconversion assay. In some embodiments, this measuring the optical signal can include removing the cartridge from the incubator or agitation system with a robotic gripper and using the optical system to inspect the wells. As discussed herein, in some cases, the optical system can deliver light of a certain wavelength (e.g., about 560 nm) to excite the sample and can detect light emitted from the sample at a different wavelength (e.g., about 590 nm). Based on the level of the light intensity emitted from the sample, a presence or absence of microorganism growth can be determined for the various antimicrobial-microorganism pair in the well.

Therefore, for each antimicrobial-microorganism pair being analyzed, the system can read the optical signals from each well being tested and send an array of data to the algorithm to be processed. In some embodiments, an array includes signals from each of the wells in 2-fold dilution series and the 3 control wells (e.g., positive, no growth, and FIT). The array for a given antimicrobial can include both metabolic redox and end point assays. The algorithm can also correct and normalize each dataset using control wells and find a relative minimum inhibitory concentration (MIC) and/or a qualitative susceptibility result (QSR) for at least one antimicrobial that reduces defined cost function. Reported MIC values then get converted into a CLSI breakpoint look up table. Conversion values can be updated each year and are found in the M100 document published by CLSI.

Alternatively or additionally, in some embodiments, one or more endpoint assays can be performed. These can comprise an assay using surface binding amplification (e.g., an indicator for time-resolved fluorescence). In some cases, the indicator can be one or more lanthanides, such as europium, strontium, terbium, samarium, and dysprosium, or any combination thereof. For example, the fluid handling system can dispense another reagent into the testing wells of the cartridge. In some cases, the fluid handling system can deliver an amount of a chemical moiety (e.g., Glutaraldehyde) and an amount of Europium-Cryptate to each well to be tested using the reagent delivery nozzles 602. Additional endpoint assay examples include, but are not limited to, the following: a metabolic assay, a surface-binding probe assay, a chemical probe assay, a biochemical probe assay, an ATP assay, a nucleic acid probe assay, a double-stranded nucleic acid probe assay, an optical density assay, a visual assay, and a pH molecular probe assay.

Once the binding amplifier is added, the cartridge can be agitated again to promote binding of the amplifier to the target microorganisms. For example, the cartridge can be placed back into the incubator 1400 or on the agitation system 1300.

After additional shaking, the samples can undergo additional separation. For example, the transfer system and lifting fingers 1202 can remove the cartridge from the incubator 1400 or agitation 1300 place it back into the centrifuge 1100 to form a pellet of microorganism. The wells can then be aspirated to remove fluid from the well. In some cases, one or more wash sequences can be performed by dispensing and aspirating a wash fluid into the well. For example, wash fluid can be dispensed into the wells using the sample wash components nozzles 603 and can be aspirated from the wells using the aspiration nozzles 604. The wash and aspiration sequences can help to remove unbound reagent and other fluids or particles from the wells and reduce nonspecific binding, which can be useful to increase signal-to-noise ratio and produce better optical results during interrogation by the optical system.

While various embodiments have been described herein, it should be understood that they have been presented and described by way of example only, and do not limit the claims presented herewith to any particular configurations or structural components. Thus, the breadth and scope of a preferred embodiment should not be limited by any of the above-described exemplary structures or embodiments, but should be defined only in accordance with the following claims and their equivalents.

What is claimed:

1. An automated rapid antimicrobial susceptibility testing system for performing a multi-assay testing sequence, the system comprising:
    one or more automated incubation assemblies comprising a nest assembly adapted to: i) house at least one test panel having a plurality of wells for receiving a sample comprising microorganisms, and ii) facilitate incubation of one or more test panels in order to undergo the multi-assay testing sequence:
    one or more agitation systems configured to generate a repeated motion of the nest assemblies;
    a centrifugation system configured to separate microorganisms from a remainder of one or more samples or diluents within the plurality of wells of the test panel by applying a relative centrifugal force of about 2000 g to about 5000 g to the test panel, thereby forming a pellet of the microorganisms within each of the plurality of wells of the test panel;
    a robotic handling assembly configured to accept one or more incoming test panels and move them between two assemblies of the system and/or between an assembly and the centrifugation system between steps of the multi-assay testing sequence;
    an automated liquid handling assembly configured to exchange one or more fluids in the plurality of wells of the test panels, wherein the liquid handling assembly comprises at least one liquid addition system and an aspiration system and wherein the aspiration system is configured to remove fluid from a portion of a well of the test panel that is away from the pellet formed by the centrifugation system; and
    an optical assembly for interrogation and readout of each assay of the multi-assay testing sequence being performed in the plurality of wells.

2. The system of claim 1, wherein:
    at least one nest assembly comprises a tiered frame comprising one or more floors, each floor comprising:
    a stage to accommodate a test panel;
    one or more cartridge positioning features extending from the stage; and
    a set of recesses to accommodate a test panel handling device; and
    the agitation system is configured to generate a repeated motion of the tiered frame.

3. The system of claim 2 wherein the tiered frame comprises multiple floors where each floor comprises at least one surface to accommodate at least one test panel.

4. The system of claim 2 wherein each floor comprises a heating element disposed in or along the stage.

5. The system of claim 1 wherein incubation system assembly is heated using forced air.

6. The system of claim 1 wherein the agitation system comprises a rotational agitation system comprising a rotating oscillating component.

7. The system of claim 6 wherein the agitation system comprises one or more linear bearing surfaces.

8. The system of claim 7 wherein the agitation system comprises two linear bearing surfaces positioned substantially perpendicularly with respect to one another and the agitation system comprises two sliding stages configured to slide along the bearing rails.

9. The system of claim 8 wherein the agitation system is configured to agitate the nest assembly along an orbital path having a radius that is about 1 mm to about 12 mm.

10. The system of claim 1 wherein the agitation system is configured to agitate the nest assembly along an orbital path and to vary a radius of the orbital path of agitation.

11. The system of claim 1 wherein the agitation system is configured to agitate the nest assembly along an orbital path at a rate of about 50 revolutions per minute to about 650 revolutions per minute.

12. The system of claim 1 wherein the robotic handling assembly is configured to move test panels between at least one of the one or more automated incubation assemblies and the optical assembly.

13. The system of claim 1 wherein the robotic handling assembly is configured to move test panels between at least one of the one or more automated incubation assemblies and an area accessible by the automated liquid handling assembly.

14. The system of claim 1 wherein reagents are stored in a disposable container.

15. The system of claim 1 wherein the optical assembly is configured to measure at least one of absorbance, fluorescence, luminescence, time-resolved fluorescence, or time-gated luminescence emitted from the sample during the multi-assay testing sequence.

16. The system of claim 15 wherein an excitation wavelength to generate a fluorescence emission is from about 545 nm to about 575 nm and a wavelength of the emission is from about 570 nm to about 610 nm.

17. The system of claim 15 wherein an excitation wavelength to generate a time-gated luminescence emission is about 280 nm to about 360 nm and a wavelength of the emission is one or more of the following: about 545 nm, about 565 nm, from about 608 nm to about 623 nm, or about 645 nm.

18. The system of claim 1 wherein the system is configured to yield a testing sequence throughput of at least 2, at least 4, at least 6, at least 8, at least 10, at least 12, at least 16, or at least 20 test panels per hour.

19. The system of claim 1 wherein a time duration for processing a test panel through the testing sequence from insertion of the test panel into the system to obtaining a result is less than 8 hours, less than 6 hours, less than 5 hours, less than 4 hours, less than 3 hours, or less than 2 hours.

20. The system of claim 1 wherein the fluid handling assembly comprises a manifold fluidly connected to at least one of the liquid addition system or the aspiration system, the manifold being configured to dispense and/or aspirate fluid using at least 8 tips.

21. The system of claim 1, wherein the test panel comprises:
- a first set of wells, comprising
  - a growth well receiving a nutrient broth and the sample; and
  - a no-growth well receiving the nutrient broth but not the sample; and
- a second set of wells, comprising:
- a plurality of antimicrobials, each antimicrobial applied to a plurality of wells in a dilution series.

* * * * *